United States Patent
Boutros et al.

(10) Patent No.: US 9,062,114 B2
(45) Date of Patent: Jun. 23, 2015

(54) GPR177 AS TARGET AND MARKER IN TUMORS

(75) Inventors: Michael Boutros, Heidelberg (DE); Iris Augustin, Dossenheim (DE)

(73) Assignees: DEUTSCHES KREBSFORSCHUNGSZENTRUM, Heidelberg (DE); RUPRECHT-KARLS-UNIVERSITAET-HEIDELBERG, Heidelberg (DE)

( * ) Notice: Subject to any disclaimer, the term of this patent is extended or adjusted under 35 U.S.C. 154(b) by 0 days.

(21) Appl. No.: 14/112,296

(22) PCT Filed: Apr. 18, 2012

(86) PCT No.: PCT/EP2012/057058
§ 371 (c)(1),
(2), (4) Date: Jan. 17, 2014

(87) PCT Pub. No.: WO2012/143382
PCT Pub. Date: Oct. 26, 2012

(65) Prior Publication Data
US 2014/0227276 A1    Aug. 14, 2014

(30) Foreign Application Priority Data
Apr. 18, 2011    (EP) .................................. 11162877

(51) Int. Cl.
| C07K 16/30 | (2006.01) |
| A61K 39/395 | (2006.01) |
| C07K 14/72 | (2006.01) |
| C07K 16/28 | (2006.01) |
| C12N 15/113 | (2010.01) |
| G01N 33/50 | (2006.01) |
| G01N 33/574 | (2006.01) |
| G01N 33/74 | (2006.01) |
| A61K 31/713 | (2006.01) |

(52) U.S. Cl.
CPC .............. *C07K 16/30* (2013.01); *A61K 39/395* (2013.01); *C07K 14/723* (2013.01); *C07K 16/28* (2013.01); *C07K 2317/34* (2013.01); *C12N 15/1138* (2013.01); *G01N 33/5011* (2013.01); *G01N 33/57407* (2013.01); *G01N 33/57415* (2013.01); *G01N 33/74* (2013.01); *G01N 2333/726* (2013.01); *A61K 31/713* (2013.01); *A61K 39/39558* (2013.01); *G01N 33/5041* (2013.01); *G01N 33/57492* (2013.01)

(58) Field of Classification Search
CPC ..................... A61K 39/395; A61K 39/39558
See application file for complete search history.

(56) References Cited

U.S. PATENT DOCUMENTS

| 7,682,607 B2 * | 3/2010 | Rhee et al. ............... 424/130.1 |
| 7,713,526 B2 * | 5/2010 | Rhee et al. ............... 424/143.1 |
| 8,507,442 B2 * | 8/2013 | Gurney et al. ............. 514/19.3 |
| 8,716,243 B2 * | 5/2014 | Zheng ....................... 514/21.2 |
| 2011/0033430 A1 * | 2/2011 | Chien et al. .............. 424/93.21 |

FOREIGN PATENT DOCUMENTS

| WO | 2006/097336 A2 | 9/2006 |
| WO | WO 2006097336 A2 * | 9/2006 |

OTHER PUBLICATIONS

Belenkaya et al., Dev. Cell, 14 (2008), pp. 120-131.*
Franch-Marro et al. Nat. Cell Biol., 10:170-177 (2008).*
An, Z., "Monoclonal antibodies—a proven and rapidly expanding therapeutic modality for human diseases," Protein Cell, 1(4):319-330, 2010.
Little, M., et al., "Of mice and men: hybridoma and recombinant antibodies," Immunology Today, 21(8):364-370, Aug. 2000.
Bartscherer K et al: "Secretion of Wnt ligands requires Evi, a conserved transmembrane protein", Cell, Cell Press, US, vol. 125, No. 3, May 5, 2006, pp. 523-533, XP002385896.
Barker Nick et al: "Mining the Wnt pathway for cancer therapeutics", Nature Reviews. Drug Discovery, Nature Publishing Group, GB,vol. 5, No. 12, Dec. 1, 2006, pp. 997-1014, XP002545380.
Logan Catriona Y et al: "The Wnt signaling pathway in development and disease", Annual Review of Cell and Developmental Biology, Annual Reviews, US, vol. 20, Jan. 1, 2004, pp. 781-810.
J. Fu et al: "Reciprocal regulation of Wnt and Gpr177/mouse Wntless is required for embryonic axis formation", Proceedings of the National Academy of Sciences, vol. 106, No. 44, Nov. 3, 2009, pp. 18598-18603.
Jay Jin et al: "Expression of GPR177 (Wntless/Evi/Sprinter), a highly conserved Wnt-transport protein, in rat tissues, zebrafish embryos, and cultured human cells", Developmental Dynamics, vol. 239, No. 9, Sep. 1, 2010, pp. 2426-2434.
Korkut Ceren et al: "Trans-Synaptic Transmission of Vesicular Wnt Signals through Evi/Wntless", Cell, vol. 139, No. 2, Oct. 2009, pp. 393-404.
Jin Jay et al: "Interaction of the mu-opioid receptor with GPR177 (Wntless) inhibits Wnt secretion: potential implications for opioid dependence", BMC Neuroscience, Biomed Central, London, GB, vol. 11, No. 1, Mar. 9, 2010, p. 33.
Fu Jiang et al: "Gpr177/mouse Wntless is essential for Wnt-mediated craniofacial and brain development.", Developmental Dynamics : An Official Publication of the American Association of Anatomists Feb. 2011 LNKD DOI:10.1002/DVDY.22541 Pubmed:21246653, vol. 240, No. 2, Feb. 2011,pp. 365-371.
Augustin et al., "The Wnt secretion protein Evi/Gpr177 promotes glioma tumorigenesis", EMBO Molecular Medicine, vol. 4, No. 1, Jan. 2012, pp. 38-51.

* cited by examiner

*Primary Examiner* — Daniel C Gamett
(74) *Attorney, Agent, or Firm* — Rothwell, Figg, Ernst & Manbeck, P.C.

(57) ABSTRACT

The present invention relates to modulators of G protein-coupled receptor 177 (Gpr177) for use in the treatment, alleviation, prevention and/or diagnosis of cancer as well as to methods for the diagnosis of such cancer.

9 Claims, 28 Drawing Sheets

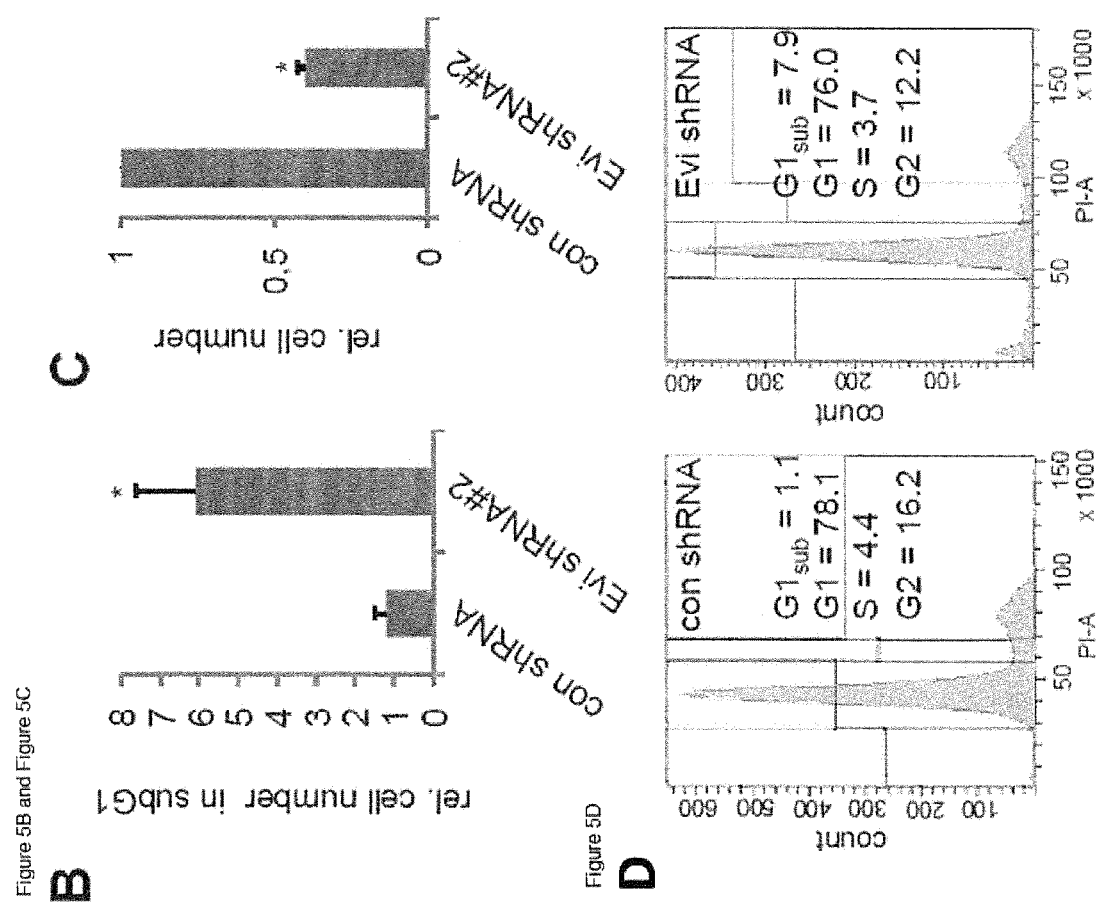

GPR177 AS TARGET AND MARKER IN TUMORS

CROSS REFERENCE TO RELATED APPLICATION

Figure 1A:
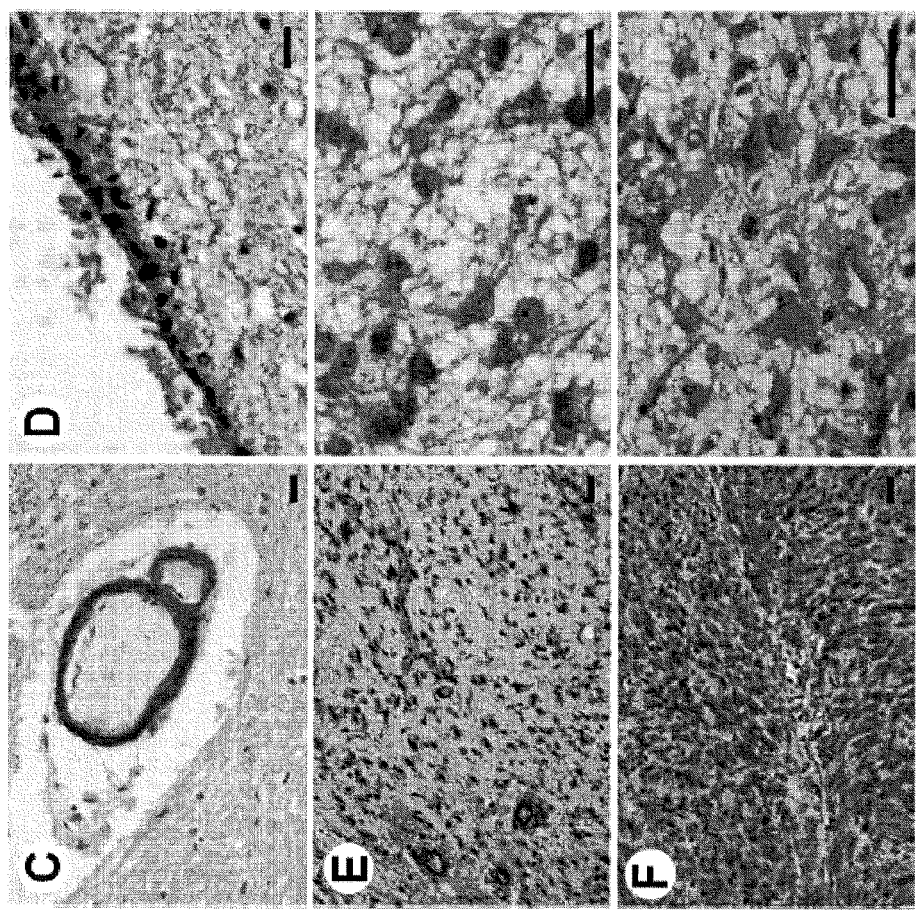

This application is a 35 U.S.C. 371 National Phase Entry Application from PCT/EP2012/057058, filed Apr. 18, 2012, which claims the benefit of European Patent Application No. 11162877.2 filed on Apr. 18, 2011, the disclosure of which is incorporated herein in its entirety by reference.

The present invention relates to modulators of G protein-coupled receptor 177 (Gpr177) for use in the treatment, alleviation, prevention and/or diagnosis of aberrant Wnt signaling, in particular cancer as well as to methods for the diagnosis of aberrant Wnt signaling, in particular cancer.

Malignant astrocytomas constitute most primary brain tumors with poor prognosis for glioma patients and low long-term survival rates. They arise de novo or develop from low CD high grade tumors and are characterized by a progressive increase in number and nature of cytogenetic aberrations. Glioblastoma, the most aggressive form, are characterized by invasive behavior, cellular heterogeneity and 'stem-cell' like behaviour. Chemoresistance towards conventional therapies frequently develops in patients and only limited treatment options are currently available.

Aberrant Wnt signaling contributes to the development of various human cancers derived from colorectal, breast, ovarian, and neuroectodermal tissues. Best characterized is its involvement in colorectal cancers. In most cases activated Wnt signaling leads to tumorigenesis as a consequence of the loss of the tumor suppressor APC. The contribution of Wnt signaling in human brain tumor was originally linked to medulloblastoma. These studies were based on Turoot syndrome, in which germline mutations in the APC gene have been identified. In addition, a range of human malignancies exhibit aberrant Wnt signaling as a result of mutations in β-catenin or Axin. Furthermore an increasing number of Wnt ligands have been associated with cellular transformation and tumor development.

Wnt/β-catenin signaling has recently been reported in astocytic tumors and aberrant activation Wnt/β-catenin signaling has been shown to correlate with brain tumor progression.

Though much is known about downstream signaling cascades in the Wnt signal receiving cell, the molecular mechanisms underlying the maturation and secretion of Wnt ligands in the Wnt producing cell are only beginning to emerge. We have recently identified Evi/Wntless/Sprinter as an essential component of the Wnt secretion machinery that encodes a highly conserved seven-pass transmembrane protein. Gpr177 is essential for Wnt secretion and loss of Gpr177 leads to accumulation of Wnt in the Wnt producing cell. Accordingly Gpr177 acts as a cargo receptor, shuttling between the Golgi and the plasma membrane and assists in Wnt cell surface presentation. Gpr177 is endocytosed and recycled to the Golgi through binding to the retromer complex. Genetic inactivation of Gpr177 in the mouse leads to embryonic lethality due to disruption of proper axial patterning.

Nineteen different Wnt molecules are transcribed by the mammalian genome. Wnt ligands have diverse and overlapping expression pattern. Some Wnt ligands are categorized according to their Wnt signaling pathway into canonical (Wnt1, Wnt3) and non-canonical Wnt (Wnt5a, Wnt11) ligands. However, a clear functional distinction of most Wnt ligands is controversial. The Wnt secretion factor Gpr177 has been shown to interact with Wnt1, Wnt3 and Wnt5a. Since it is a single-gene family in vertebrates as well as invertebrates, it is likely that Gpr177 is involved in the secretion of all Wnt proteins.

Glioma are highly aggressive brain tumors. Despite the progress in diagnosis and standard tumor therapy, glioma are still associated with a bad prognosis for the patient. Thus, new therapies and targets are urgently needed. The present invention describes a novel therapeutic target or diagnostic marker. The identification of markers and novel druggable targets of glioma remains therefore an important challenge.

Thus, according to a first aspect, the present invention relates to a modulator of G-protein coupled receptor 177 (Gpr177) for use in the treatment, alleviation, prevention and/or diagnosis of aberrant Wnt signaling, in particular cancer, most preferably brain tumors.

Herein the terms "Gpr177" and "Evi" are used interchangeable and/or synonymous.

The present invention is based on the role of Gpr177 during glioma tumorigenesis which is shown herein for the first time. Expression profiling identified barely detectable Gpr177 expression in normal brain and strong stage-independent expression of Gpr177 in human astrocytic gliomas indicating an involvement of Gpr177 even in the earliest stages of glioma tumorigenesis. Silencing of Gpr177 expression in glioma cells and glioblastoma-derived cancer stem like cells led to reduced proliferation and apoptosis.

According to the present invention Gpr177 is preferably human Gpr177, which is in particular characterized by the Genbank Accession No. NM_001002292.

In terms of the present invention, a "modulator" is a compound which increases or decreases, in other words stimulates or inhibits, the activity and/or expression of G-protein coupled receptor 177/Gpr177 compared to G-protein coupled receptor 177/Gpr177 which is not affected by the modulator.

The inhibitor according to the present invention may act on the protein level and/or on the nucleic acid level.

According to an especially preferred embodiment, the modulator according to the present invention is an inhibitor. The inhibitor may block or reduce the activity of Gpr177 and/or the expression level of Gpr177 in comparison to Gpr177 of the same tissue, which is not influenced by the inhibitor. Another embodiment relates to a stimulator. The stimulator may increase the activity of Gpr177 and/or the expression level of Gpr177 in comparison to Gpr177 of the same tissue, which is not influenced by the stimulator.

Being a transmembrane-protein Gpr177 is easily accessible for antibodies.

Thus, according to an especially preferred embodiment, the inhibitor of Gpr177 is an antibody or antibody fragment against Gpr177. Such antibodies may include, but are not limited to, polyclonal, monoclonal, chimeric single chain, Fab fragments, and fragments produced by a Fab expression library.

Antibodies according to the present invention preferably bind to the extracellular domain of Gpr177.

According to one embodiment of the invention the anti-Gpr177 antibody binds to the Wnt binding site of Gpr177, in other words inhibits the binding of Gpr177 on Wnt. Preferably the antibody according to the present invention thus binds to a section between amino acid 101 to 232 of Gpr177. The binding site of Gpr177 on Wnt is described in detail in Fu et al. (PNAS, 2009, vol. 106, no. 44, pp. 18598-18603).

According to a particularly preferred embodiment, the antibody or antibody fragment against Gpr177 recognizes and/or binds to the (a) epitope H-FTSPKTPEHEGRYYNC-OH (SEQ ID NO:1), or
(b) an epitope comprising at least 10, more preferably 8, even more preferably 5 and most preferably 3 consecutive amino acids of a) but being N- or C-terminal shifted in the corresponding Gpr177 amino acid sequence or
(c) an epitope having at least 75%, more preferably 80%, even more preferably 85%, 90% and most preferably 95% amino acid identity to the epitopes of (a) and/or (b),
or a corresponding antibody fragment.

The term antibody includes "fragments" or "derivatives", which have at least one antigen binding site of the antibody. According to a preferred embodiment the antibody or fragment thereof may be a Fab fragment, a Fab' fragment, a) F(ab° fragment, a Fv fragment, a diabody, a ScFv, an affibody, an avimer, a nanobody, a domain antibody and/or single chains.

Humanized, in particular monoclonal humanized antibodies are particular preferred.

For the production of antibodies, various hosts including goats, rabbits, rats, mice, humans, and others, may be immunized by injection with the protein or any fragment or oligopeptide thereof which has immunogenic properties. Depending on the host species, various adjuvants may be used to increase immunological response. It is preferred that the peptides, fragments or oligopeptides used to induce antibodies to the protein have an amino acid sequence consisting of at least five amino acids, and more preferably at least 10 amino acids.

Monoclonal antibodies to the proteins may be prepared using any technique that provides for the production of antibody molecules by continuous cell lines in culture.

It will be apparent to those skilled in the art that the antibodies of the invention can be further coupled to other moieties for, e.g., drug targeting and imaging applications. Coupling may be conducted chemically after expression of the antibody or antigen to site of attachment or the coupling product may be engineered into the antibody or antigen of the invention at the DNA level. Such groups may be attached by spacer arms of various lengths to reduce potential steric hindrance.

For diagnostic purposes, the antibody or antibody fragment of the invention may be coupled to a labelling group. Suitable label groups include radioactive labels, fluorescent labels, suitable dye groups, enzyme labels, chromogenes, chemiluminescent groups, biotinyl groups etc. Such labelled antibodies or antibody fragments may be in particular used in immunohistochemistry assays or for molecular imaging in vivo.

For therapeutic purposes, the antibody or antibody fragment of the invention may be conjugated with a effector group, such as a radioactive group or a cytotoxic group.

According to another preferred embodiment, the inhibitor of Gpr177 acting on the nucleic acid level may be selected from an antisense molecule, in particular short-hairpin RNAs (shRNAs), a ribozyme or an RNAi molecule, in particular short-interfering RNAs (siRNAs), small molecules and/or a low molecular weight organic molecule. shRNAs and siRNAs are in particular preferred.

According to the present invention, "small molecules" and/or "low molecular weight organic molecules" are molecules which show a molecular weight of less than 5000 Da, more preferably less than 2500 Da.

In particular, the antisense molecules may be used in situations in which it would be desirable to block the transcription of the mRNA. Thus, antisense molecules may be used to inhibit protein activity, i.e. Gpr177 activity and/or expression, or to achieve regulation of gene function. Such technology is well known in the art.

Nucleic acid inhibitor molecules, e.g. shRNAs, ribozymes or an RNAi molecules, in particular siRNAs, may be prepared by any method known in the art for the synthesis of nucleic acid molecules. These include techniques for chemically synthesizing oligonucleotides such as solid phase phosphoramidite chemical synthesis. Of course, the use of cell extracts comprising such molecules is also comprised by the present invention.

Expression vectors derived from retroviruses, adenovirus, herpes or vaccinia viruses or from various bacterial plasmids may be used for delivery of nucleotide sequences to the targeted organ, tissue or cell population.

According to claim 1, the present application relates to the treatment, alleviation, prevention and/or diagnosis of cancer.

In a preferred embodiment the cancer to be treated is cancer, which is associated with aberrant Wnt signaling and is preferably associated with enhanced Gpr177 expression. In terms of the present invention "enhanced Gpr177 expression" describes an increased expression compared with the same type of tissue, e.g. brain tissue, lung tissue, renal tissue, that is not affected by cancer.

In a preferred embodiment the cancer to be treated is selected from colon, liver, ovarian, thyroid, uterine, gastric, renal, neuroectodermal tissue cancer, melanoma and/or corresponding metastasis.

In a particularly preferred embodiment the cancer to be treated is brain tumor and/or breast tumor.

In terms of the present invention, a "brain tumor" is preferably an intracranial solid neoplasm, a tumor within the brain or the central spinal canal, wherein "tumor" is defined as any abnormal growth of cells.

According to a particular preferred embodiment, the brain tumor to be treated or diagnosed is selected from glioma, more preferably malignant astrocytoma, and in particular glioblastoma and/or medullablastoma. Glioblastoma multiforme (GBM) is the most common and most aggressive type of primary brain tumors in humans.

In another embodiment of the present invention, the modulator, in particular the inhibitor, is to be used in combination with at least one further pharmaceutical active agent suitable for the alleviation, treatment and/or prevention of cancer, particularly brain tumors, such as a further antibody or antibody fragment. Of course, active agents able to cross the blood-brain-barrier are preferred. The treatment may be combined with surgery, chemotherapy and/or radiotherapy depending on the type of tumor, age, functional status of the patient, the extent of surgical tumor removal etc.

Of course, a modulator as defined herein may be used for the preparation of a medicament for the treatment, alleviation, prevention and/or diagnosis of cancer, particularly breast and/or brain tumors, as defined above.

Another aspect of the present invention relates to a method for diagnosing cancer as defined above, particularly breast and/or brain tumors and/or for discrimination between cancerous and non-cancerous tissue, comprising the steps of determining at least the expression of Gpr177 in a sample to be analysed.

Gpr177 expression is downregulated in the adult brain. During glioma tumorigenesis the inventors observed a pronounced stage-independent expression of Gpr177. Thus, by the method of the present invention it has become possible to determine even minor neoplastic changes.

According to a preferred embodiment, an increased expression of Gpr177 does not depend on the degree of malignancy. Age, gender, p53 mutation, IDH mutation, and the MGMT methylation status of a patient did not influence on the expression of Gpr177 the tumors that have been examined.

According to another embodiment, Gpr177 is expressed in both low and high grade glioma. In general and without being limited to this statement, tumors expressing Gpr177 show a poor prognosis.

Moreover, it is indicated that Gpr177 is functionally involved in glioma tumorigenesis and tumor progression. The analysis of Gpr177 during glioma tumorigenesis identified Gpr177 as a robust diagnostic marker of human gliomas and established a functional role of Gpr177 in the pathogenesis of human brain tumors. The diagnostic method of the invention may be used to distinguish between absence, presence, and excess gene expression, and to monitor regulation of protein levels during therapeutic intervention.

Further steps which may be comprised by the method of the present invention are, of course, providing a sample to be analysed, such as for example from a histological examination, and/or comparing the expression of Gpr177 in the sample to be analysed with a control such as Gpr177 expression in non-affected tissues, for example tissues of healthy humans not suffering from a corresponding type of cancer.

According to a preferred embodiment, the expression of Gpr177 is determined by immunohistochemical methods. However, of course each method capable of measuring the activity of a given protein or the amount of expression such as RNA-based methods may be applied. Preferably, the antibody described herein or a corresponding antibody fragment is used. Of course, the antibody provided by the present invention and/or described as above can be used.

The method according to the present invention may be combined with other diagnostic methods such as any serum-based methods. In particular it may be used to give a definitive prognosis of brain tumor after non-invasive methods such as electrophysiological, ophtamological and/or otolaryngological examinations.

Another aspect of the present invention relates to a pharmaceutical composition comprising at least one inhibitor of Gpr177. Preferably, the inhibitor selected from the group consisting of an antibody against Gpr177 as described herein or a corresponding antibody fragment against Gpr177, an antisense molecule, in particular shRNAs, a ribozyme or an RNAi molecule, in particular siRNA, a low molecular weight organic molecule or any combination thereof, as described above in detail.

The composition preferably comprises an pharmaceutically acceptable carrier, diluent and/or excipient. Examples of suitable pharmaceutical carriers, excipients and/or diluents are well known in the art and include phosphate buffered saline solutions, water, emulsions, various types of wetting agents, sterile solutions etc. Further details on techniques for formulation and administration may be found in Remington's Pharmaceutical Sciences (Maack Publishing Co., Easton, Pa.).

Furthermore, the pharmaceutical composition of the invention may comprise further agents depending on the intended use of the pharmaceutical composition. According to an especially preferred embodiment, the pharmaceutical composition of the present invention comprises at least one further pharmaceutically active agent.

Administration of the suitable compositions may be effected by different ways known to the person skilled in the art, e.g., by oral, intravenous, intraperitoneal, subcutaneous, intramuscular, topical, intradermal, intranasal or intrabronchial administration. Preferred is an intravenous, intramuscular and/or subcutaneous administration.

These pharmaceutical compositions can be administered to the subject at a suitable dose. The dosage regimen can be determined by the attending physician and clinical factors.

The compositions of the invention may be administered locally, in particular at the site of the tumor to be treated and/or the surgery site after a tumor has been removed, or systemically. Preparations for parenteral administration include sterile aqueous or non-aqueous solutions, suspensions, and emulsions. Preservatives and other additives may also be present such as, for example, antimicrobials, antioxidants, chelating agents, and inert gases and the like.

A further aspect of the present invention relates to an antibody against Gpr177, recognizing and/or binding (a) epitope H-FTSPKTPEHEGRYYNC-OH (SEQ ID NO:1), or
(b) an epitope comprising at least 10, more preferably 8, even more preferably 5 and most preferably 3 consecutive amino acids of a) but being N- or C-terminal shifted in the corresponding Gpr177 amino acid sequence or
(c) an epitope having at least 75%, more preferably 80%, even more preferably 85%, 90% and most preferably 95% amino acid identity to the epitopes of (a) and/or (b).

In particular, the antibody may be a monoclonal antibody or a polyclonal antibody.

A further aspect relates to a method of screening for an agent for the diagnosis, alleviation, treatment and/or prevention of aberrant Wnt signaling, in particular cancer, preferably breast cancer and/or brain tumor such as malignant astrocytoma and/or gliobastoma, comprising the steps of (a) providing a cell capable of expressing G protein-coupled receptor 177 or/and providing a cell extract or sample, preferably a brain cell extract or sample containing G protein-coupled receptor 177,
(b) contacting a candidate agent with the cell and/or the cell extract or sample,
(c) determining the amount and/or the activity G protein-coupled receptor 177 and
(d) selecting a candidate agent which reduces the amount and/or activity of the G protein-coupled receptor 177.

Candidate agents may be found among biomolecules including peptides, antibodies, saccharides, fatty acids, steroids, purines, pyrimidines, nucleic acids, in particular RNAi molecules, and derivatives, structural analogues or combinations thereof. Candidate agents may be obtained from a wide variety of sources including libraries of synthetic or natural compounds. Of particular interest are screening assays for agents that have a low toxicity for mammalian cells.

Of course, the inventive methods can be carried out in a high-throughput fashion.

Finally, the invention also relates to a kit comprising at least an inhibitor of Gpr177, in particular an antibody against Gpr177, as defined herein The kit may be used for diagnostic or therapeutic purposes or for screening applications as described above. The kit may further contain user instructions.

FIGURE LEGENDS

Figure 1A:
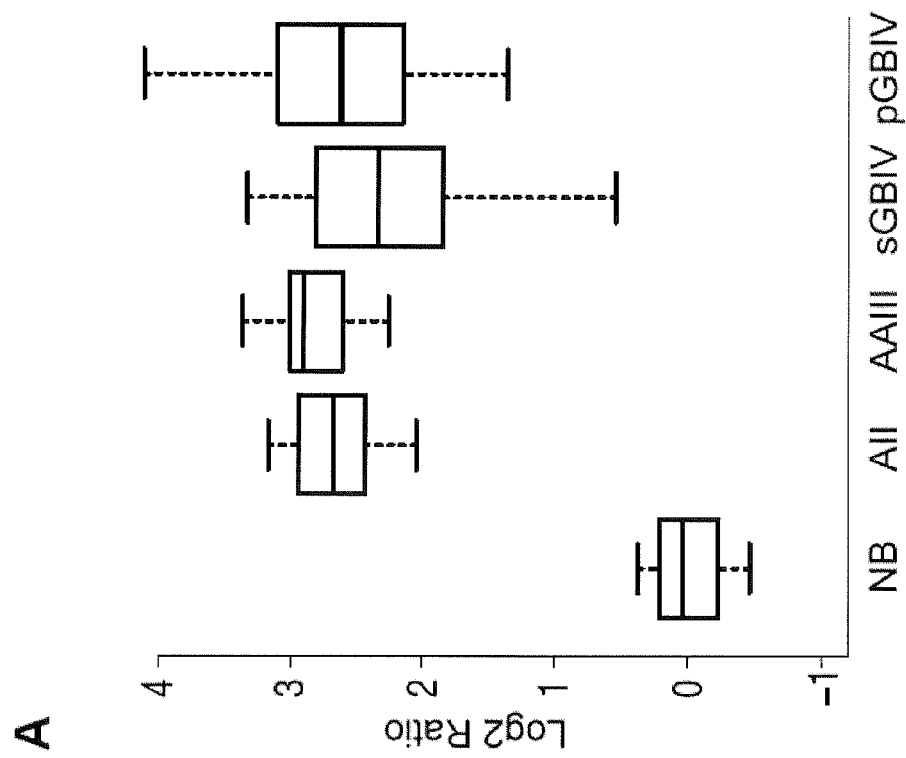

FIG. 1: Gpr177 expression in astrocytomas. (A) Log2 gene expression ratios normalized to the mean expression in normal brain (NB) samples are shown for astrocytoma WHO grade II (AII), anaplastic astrocytoma WHO grade III (AAIII), secondary glioblastoma WHO grade IV (sGBIV) and primary glioblastoma WHO grade IV (pGBIV). Median RNA expression is indicated by horizontal bars; boxes show the 25th and 75th percentile range, whiskers mark the 5th and 95th percentiles; maximum and minimum values are depicted as horizontal bars. (B) The specificity of the antibody against Gpr177 was confirmed by siRNA silencing of the target protein. U87MG cells were transfected with three independent siRNAs to silence Evi. Silencing of gene expression was validated by Western blot and quantified real-time RT-PCR confirming robust downregulation of Gpr177 expression with all siRNAs. β-Actin was detected as loading control. PCR-data are expressed as mean±SD of 3 independent experiments. (C-F) Representative immunohistochemical stainings for Gpr177 on tissue sections of normal brain and different grade astrocytic glioma. (C) Normal brain, Evi-positive ependymal cells; (D) Normal brain, Evi-positive vascular smooth muscle cells; (E) Evipositive tumor cells in astrocytoma grade II, left and right; (F) Evi-positive tumor cells in primary glioblastoma multiforme, left and right. Scale bar: 100 μm FIG. 2: Volcano plot showing measurements resulting from LIMMA analysis for differential expression of Gpr177 versus control. (A) The graph, shows the correlation between the two distinct siRNAs Evi#1 and Evi#3. This shows the replication between these two siRNAs is high ($R^2=0.99$), with no obvious off target effects. (B) Plotted on the x-axis is a measure of log2Fold change against the significance of this change (log odds ratio) on the yaxis. Points highlighted in red have a log odds ratio>=10. (C) The relative mRNA expression levels of IL6, IL8 and Gpr177 after Gpr177 silencing analyzed by quantified RT-PCR. Data are expressed as mean±SD of 3 independent experiments.

Figure 3:
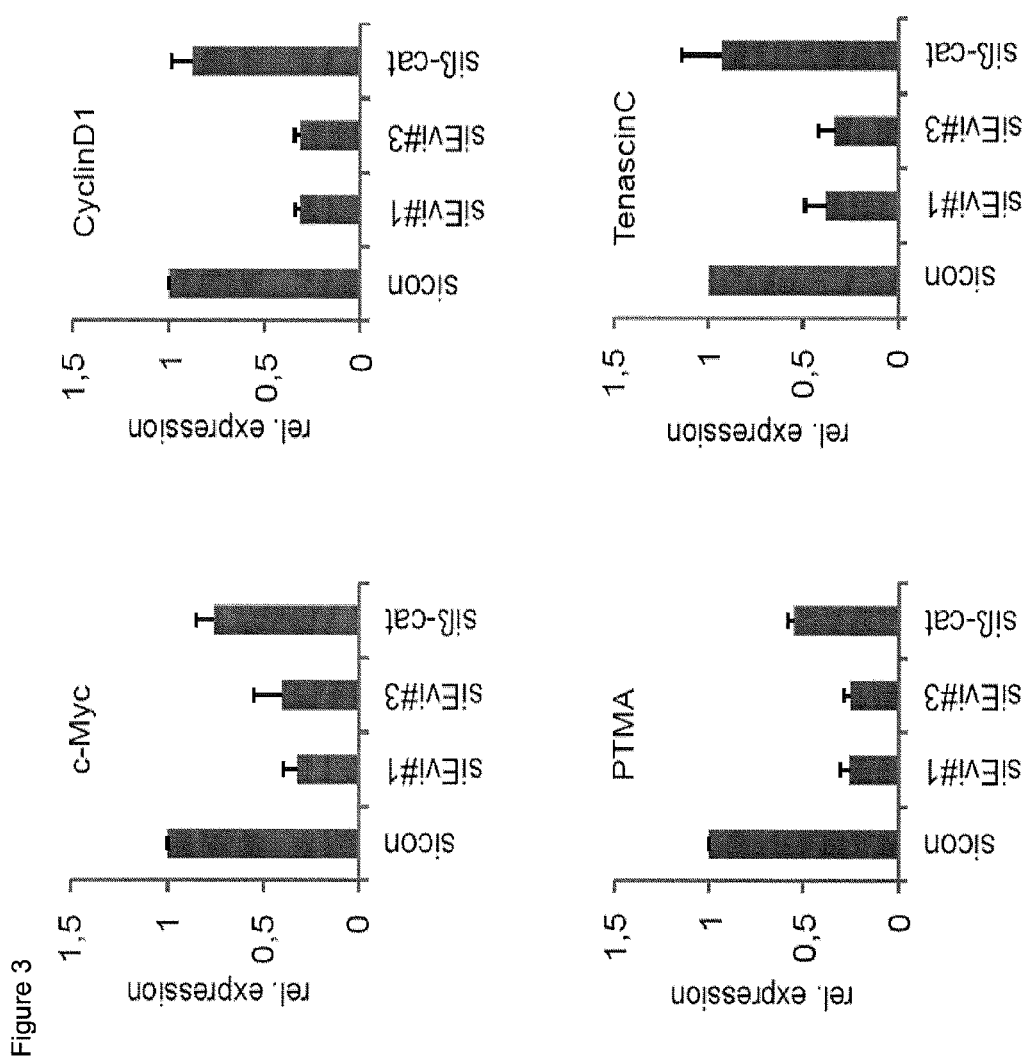

FIG. 3: Expression of pro-proliferative genes in U87MG cells after Gpr177 silencing. Cells were transduced with indicated siRNAs. The relative mRNA expression levels of Cyclin D1, c-Myc, PTMA and Tenascin-C were analyzed by quantified RT-PCR. Data are expressed as mean±SD of 3 independent experiments.

FIG. 4: Effect of RNAi-mediated silencing of Gpr177 and β-catenin expression on the proliferation of glioblastoma cell lines. (A) Proliferation of Gpr177 RNAi transduced U87MG cells and A172 cells is reduced compared to control siRNA transduced cells. β-catenin silencing has no significant effect on proliferation than Evi. Gpr177 and β-catenin silencing has no significant effect on proliferation of T98G cells. (B) Gpr177 shRNA transduced cells show reduced proliferation capacity compared to shRNA control U87MG cells. (C) Gpr177 silencing causes reduced colony formation in U251 cells. Representative example of 3 independent experiments is shown (right). Data are expressed as mean±SD of 3 independent experiments. (D) Gpr177 downregulated U87MG cells have more cells in G1 phase and less in S phase compare to control cells. Change of cell shape after down regulation of Gpr177 (C, right). Pictures were taken the day of seeding and therefore cell number differences can not yet be seen.

FIG. 5: Silencing of Gpr177 expression induces apoptosis in glioblastoma-derived cancer stem like cells. (A) Neurosphere shape and size is disturbed after Gpr177 silencing. Scale bar 100 μm (B) Lentiviral shRNA silencing of Gpr177 expression in NCH421k cells leads to an increase in the sub-G1 fraction and (C) reduction in cell number compared to control transfected spheres. (D) Representative graphs of cell cycle distribution. Data are expressed as mean±SD of 3 independent experiments.

Figure 6A:
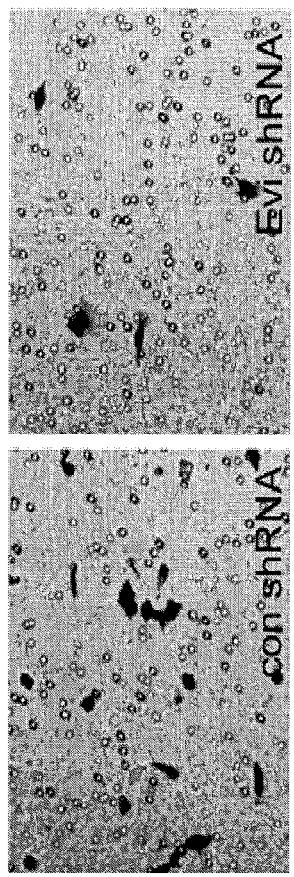
Figure 6A:
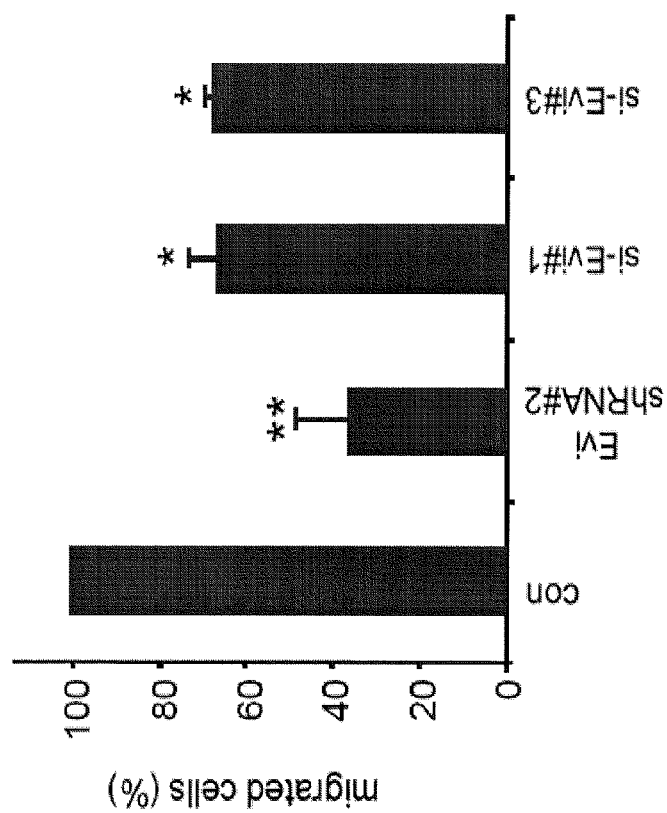

FIG. 6: Effect of Gpr177 silencing on migration and tumor xenografts. (A) Gpr177 shRNA U87MG cells show less transwell migration compared to control. Similar effect is achieved by siRNA transfection. Values represent mean±SD from 3 independent experiments. (B) Antiglioma formation of shRNA targeting Gpr177 in vivo. The appearance of xenograft subcutaneous U87MG glioma in Gpr177 shRNA and control treated cells was reduced in Gpr177 downregulated glioma.

Figure 7:
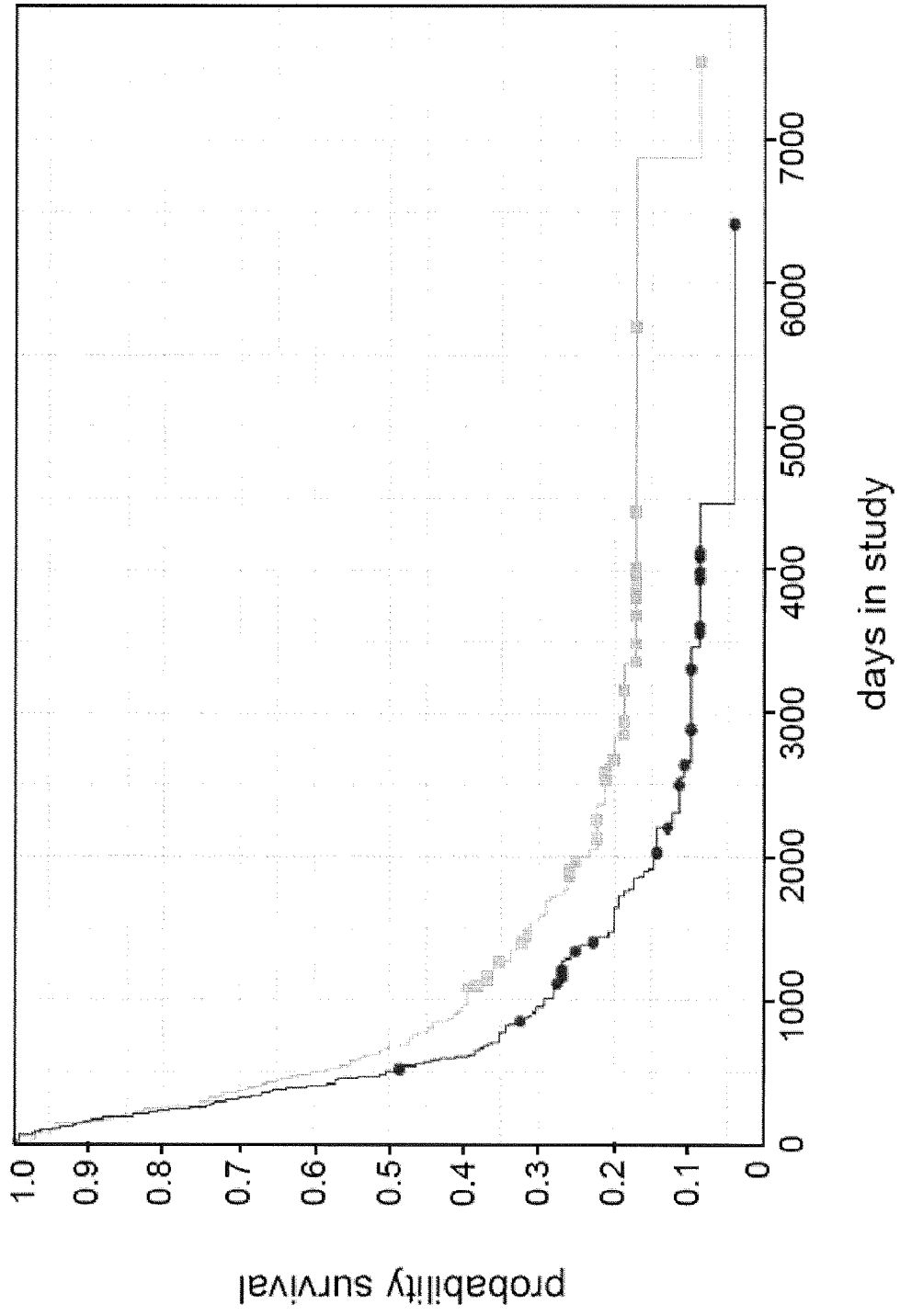

FIG. 7: Tumors that overexpress Gpr177 show a poor prognosis. Kaplan Meier analysis showing the association of Gpr177 expression with overall survival of glioma patients. Results were obtained form database of National Cancer Institute. 2005. REMBRANDT home page. <http://rembrandt.nci.nih.gov>. Accessed 2010 Dec. 6. Red line indicates more than 2-fold upregulation (187 patients), yellow-line indicates patients with 0.5-2-fold increased Gpr177 expression (154 patients). Downregulated samples are not includes because of insufficient sample numbers in this group (2 patients). P-values=0.013.

FIG. 8: Expression of Gpr177 and Wnt ligands in glioma cell lines. (A) Immunocytochemical detection localizes Gpr177 to the cytosol with enriched expression in perinuclear regions. Silencing of Gpr177 expression excludes Gpr177 staining in siRNA-targeted U87MG cells. (B) Copy number of Gpr177 in T98G, A172, U87MG, 0251 cell lines was evaluated by quantified real-time RT-PCR. (C) Expression profile of 19 Wnt molecules in U87MG cells was determined by IIlumina human HT12 chip analysis.

Figure 9:
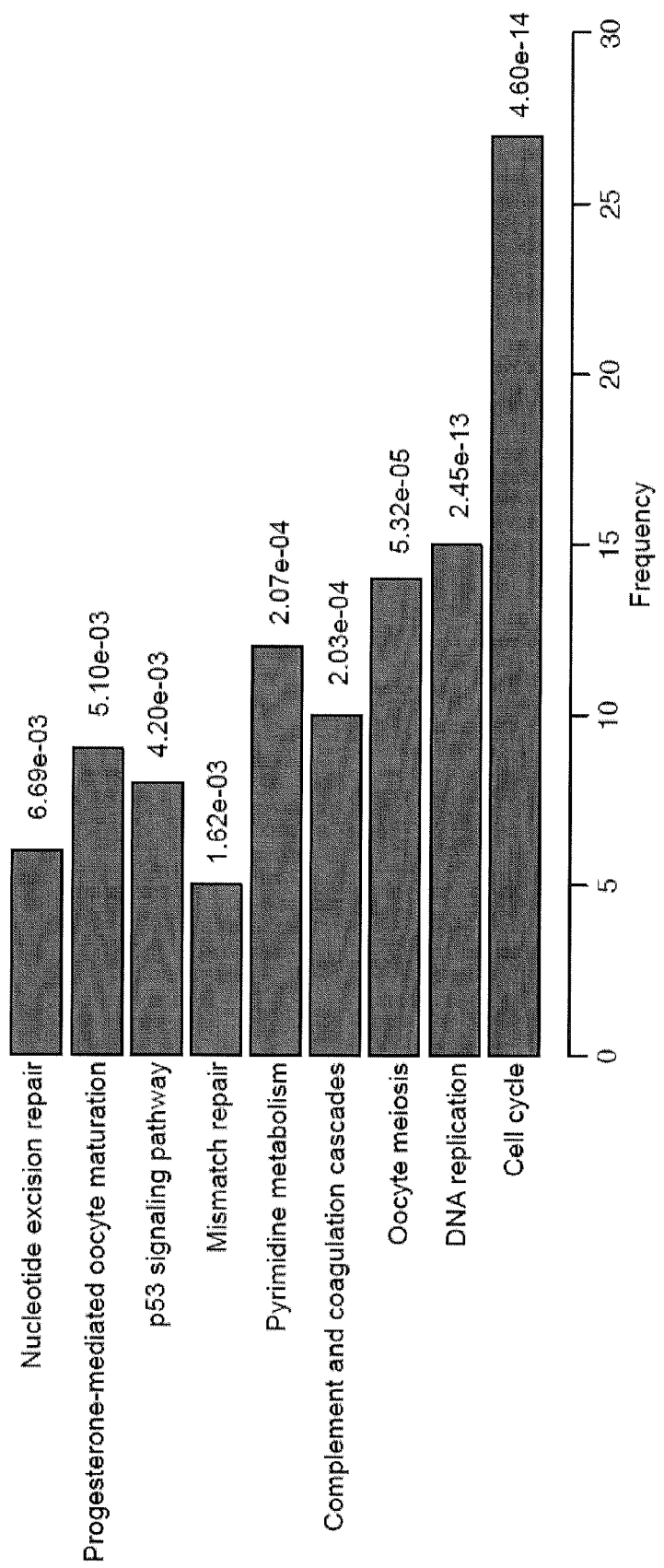
Figure 10A:
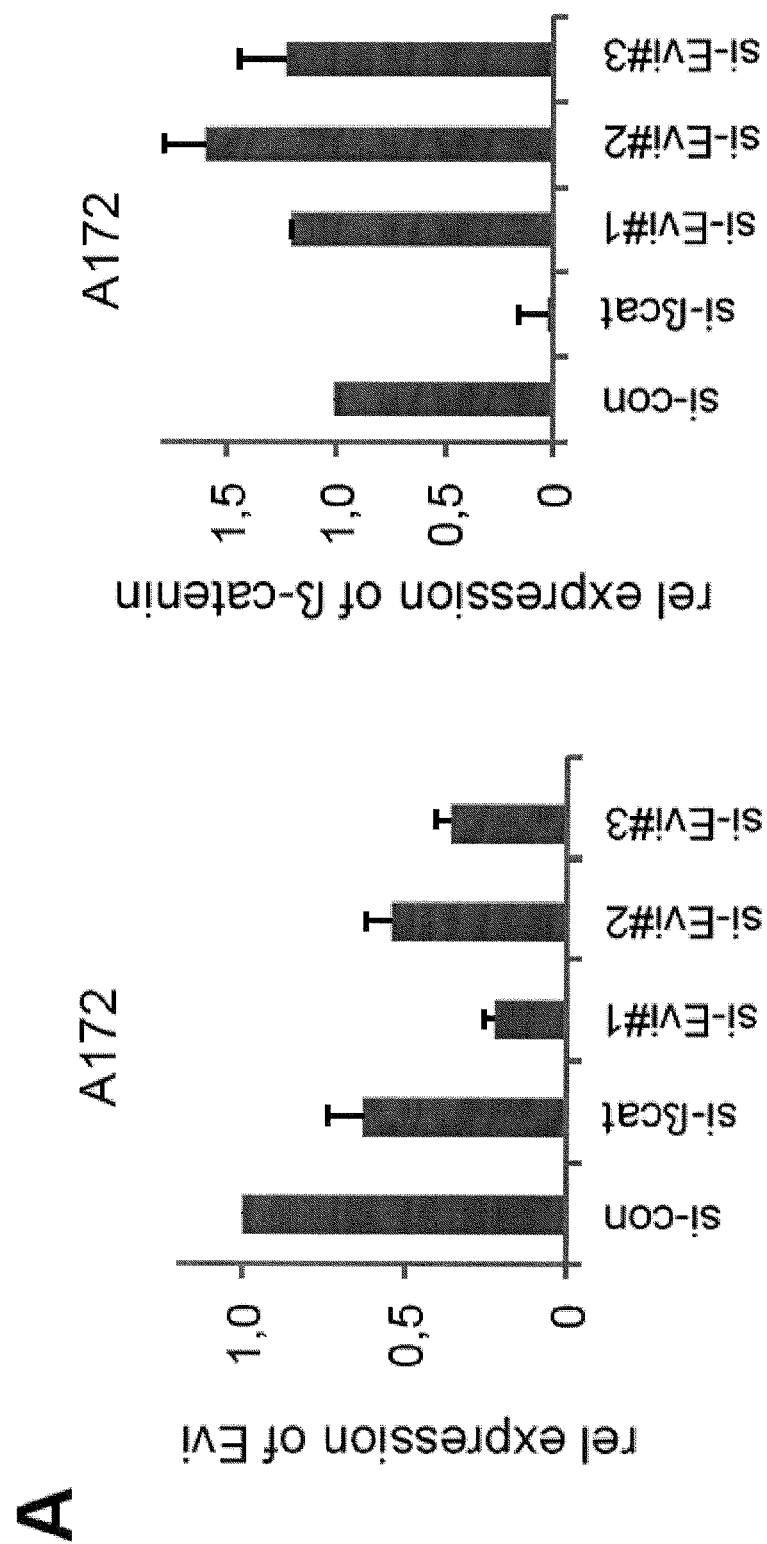
Figure 10A:
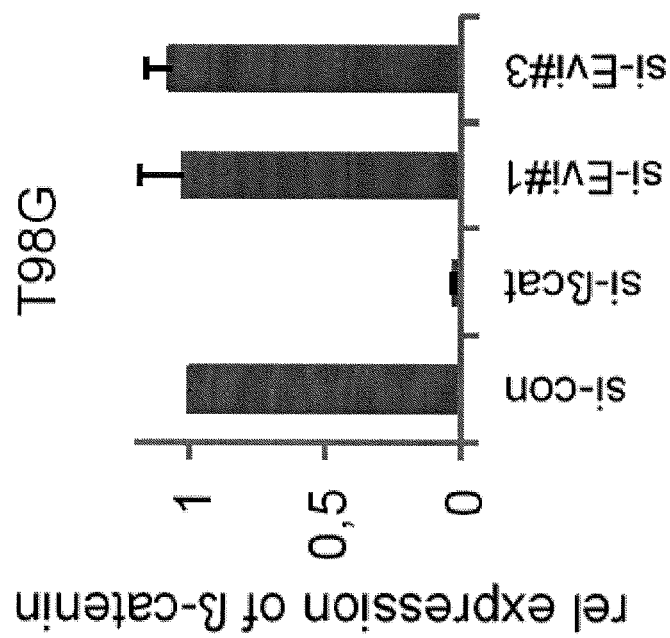
Figure 10A:
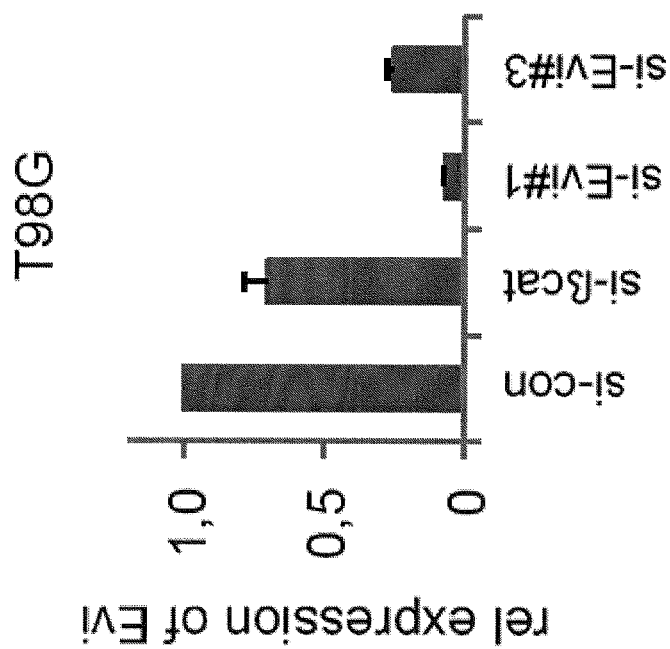
Figure 10A:
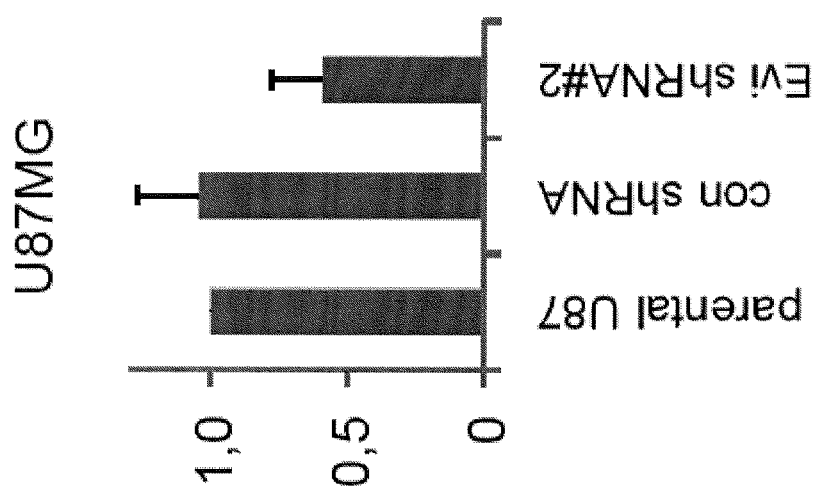
Figure 10A:
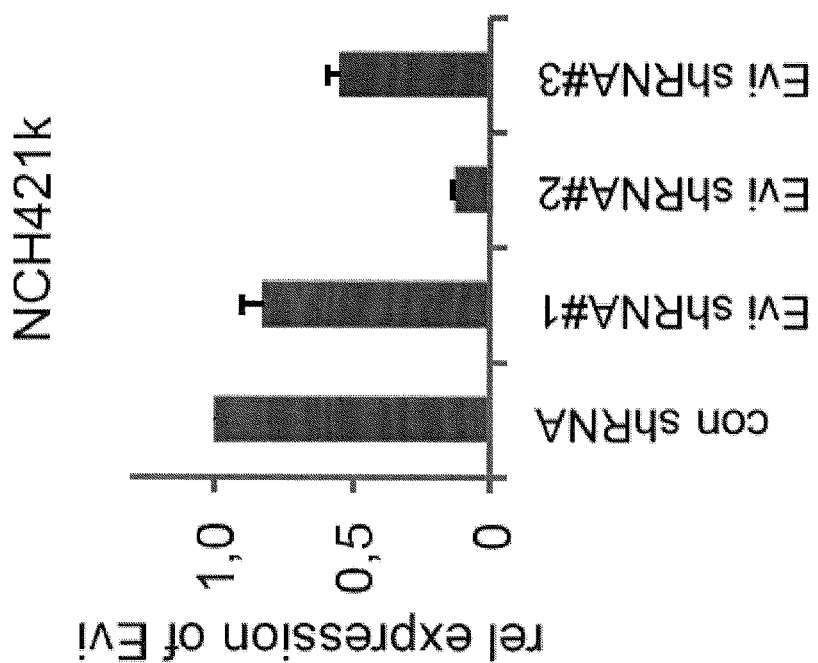
Figure 10B:
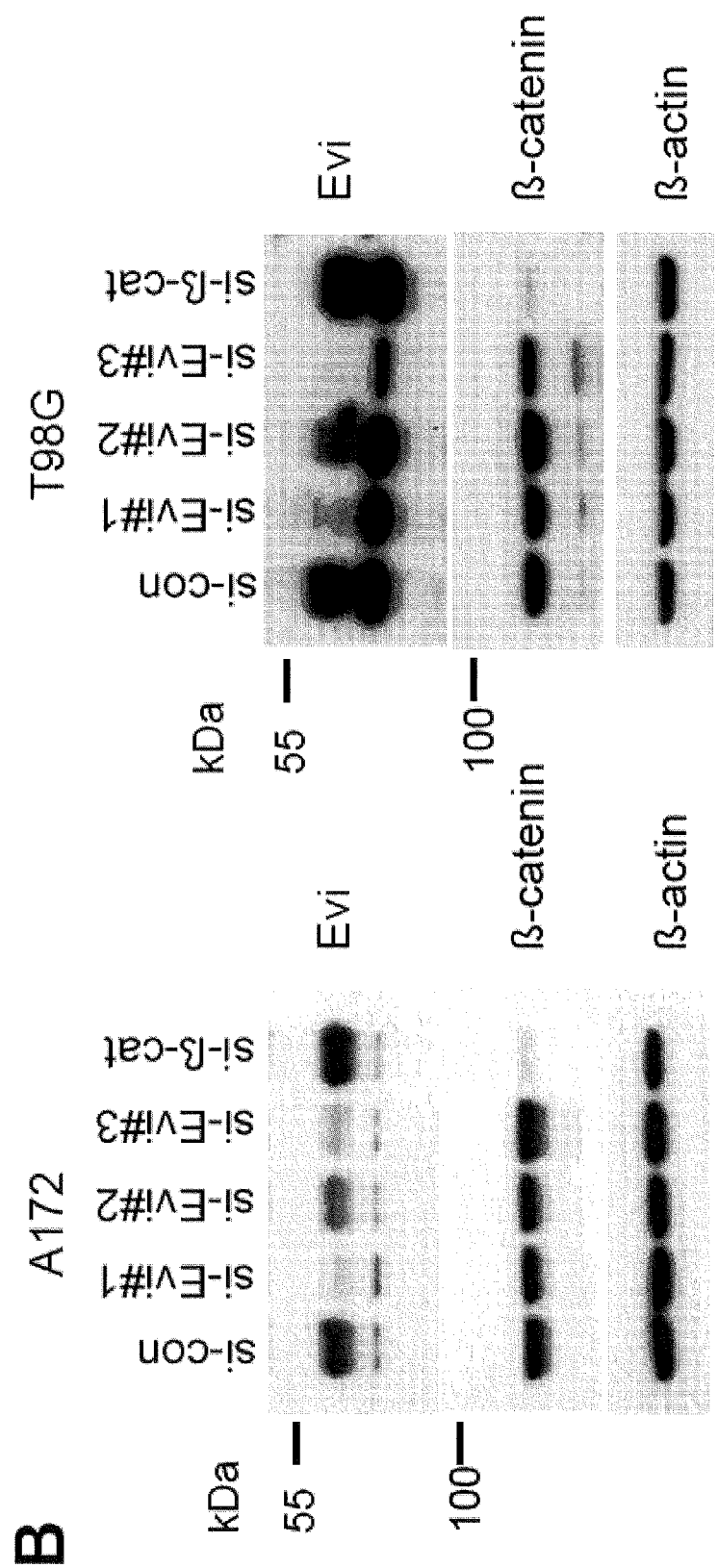
Figure 10B:
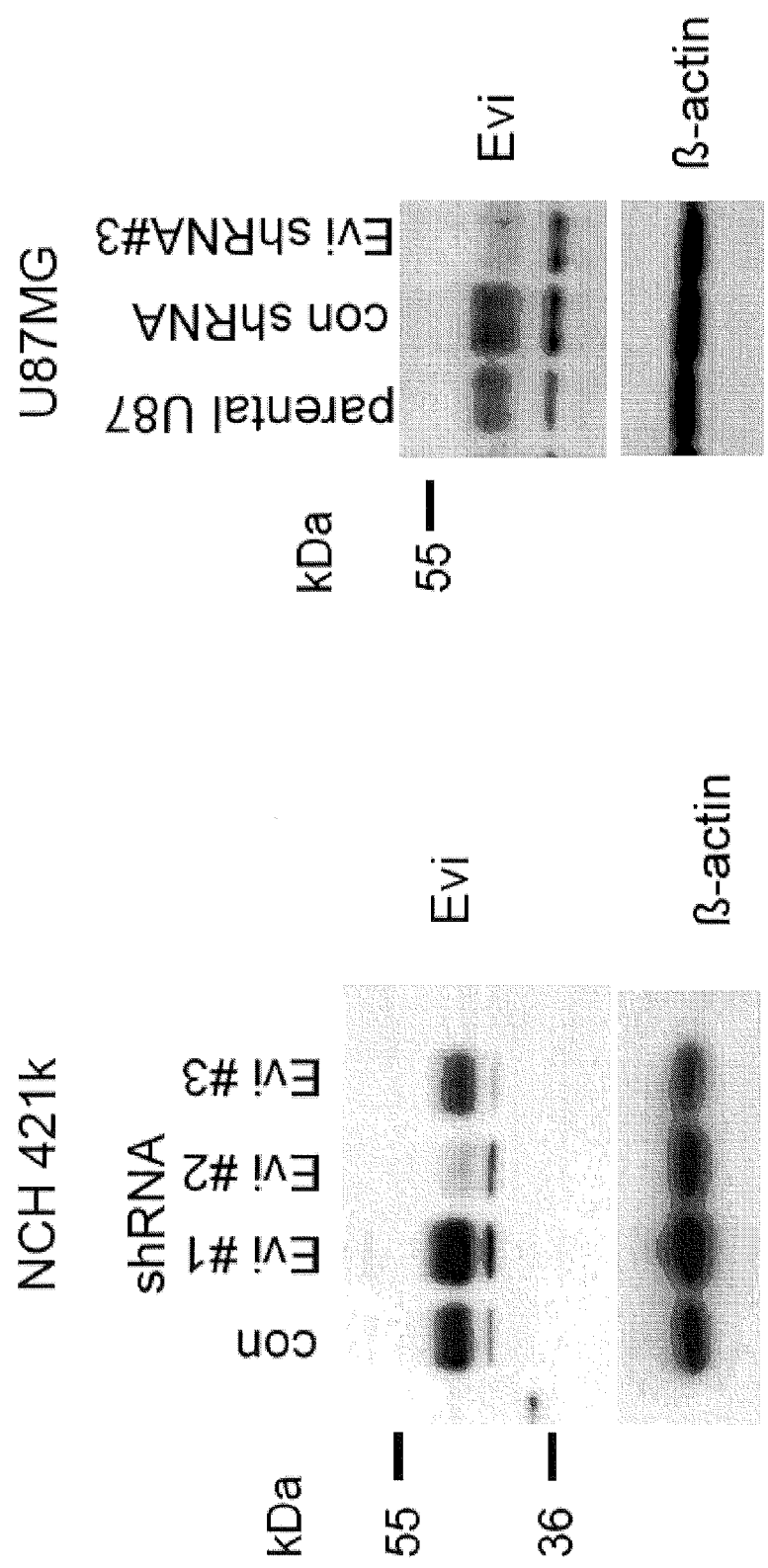

FIG. 9: Over-represented KEGG categories in set of differentially expressed genes (Fisher's exact test, p<0.01). The length of the bars represents the number of genes within the set of differentially expressed genes that are annotated as part of the corresponding KEGG category. The numbers is red indicate the significance of the over-representation. The KEGG categories are not mutually exclusive. "Cell cycle" is the most significant over-represented category.

FIG. 10: (A) Cells were transduced with indicated siRNAs and knock down efficiencies were determined by quantified real-time RT-PCR. Values represent mean±SD from 3 independent experiments. (B) Western Blot analysis after Gpr177 and β-catenin silencing. β-Actin was detected as loading control. Representative example of at least 3 independent experiments is shown.

FIG. 11: Effect of Gpr177 and β-catenin siRNA transduction in U251, LN229 and LN18 cells. (A) Proliferation of Gpr177 RNAi transduced U251 cells is reduced compared to control siRNA transduced cells. (B, C) Verification of Gpr177 and β-catenin silencing by quantified real-time RT-PCR and Western Blot analysis. (D) Proliferation of Gpr177 RNAi transduced LN229 and LN18 cells is reduced compared to control siRNA transduced cells. (E) Verification of Gpr177 silencing by quantified real-time RT-PCR. Values represent mean±SD from 3 independent experiments.

EXAMPLES

Materials and Methods
Cell Lines and Tumor Models

Human glioblastoma multiform-derived U87MG, A172, T98G, U251, LN18 and LN29 cells were by Dr. W Roth and Dr. P. Angel (Heidelberg). Cells were grown as monolayers in Dulbecco's modified Eagle's medium (DMEM) with 10% fetal bovine serum (Invitrogen) and 37° C. and 5% $CO_2$ in a humidified atmosphere. The investigated brain CSC line, NCH421k, was established from primary glioblastoma patients undergoing surgical resection according to the research proposals approved by the Institutional Review Board at the Medical Faculty University of Heidelberg, The brain CSC line was characterized genotypically and phenotypically in a previous study (Campos et al, 2010). NCH421k was cultivated at 37° C. in a humidified incubator with 5% $CO_2$, as flowing aggregates (neurospheres) on uncoated tissue culture dishes. Brain CSC medium consisted of Dulbecco's modified Eagle medium/F-12 medium containing 20% BIT serum-free supplement, basic fibroblast growth factor (bFGF) and epidermal factor (EFG) at a concentration of 20 ng/ml each (all Provitro, Berlin, Germany).

Mission RNAi clones targeting Gpr177 were obtained from Sigma-Aldrich (TRCN0000133858 [Gpr177 shRNA#1], TRCN0000138901 [Gpr177 shRNA#2], TRCN0000138525 [Gpr177 shRNA#3], Mission Non-Target shRNA Control Vector). Lentiviral particles were produced according to the manufacturer's instructions (Sigma-Aldrich). Produced lentiviruses were concentrated by ultra centrifugation using SW41 rotor (Beckman, Coulter, Fullerton, Calif., USA). Titer was measured by detecting GFP positive HEK293T cells using flow cytometry. before transduction, neurospheres were dissociated by trypsinization. Transductions were performed at 5 of multiplicity of infection (MO1-5), conferring ~90% transduction efficiency without significant cytotoxicity in negative control samples. Stable infected glioblastom cell lines were selected in a medium containing 1 µg/ml puromycin (Invitrogen). Stable cell lines were maintained as polyclonal cell populations.

Transient siRNA transfections of all cell lines were conducted using Dharmafect Reagent (ThermoFisher), siRNAs using human Evi, β-catenin and control siRNAs had the targeting sequences:

```
ACGAAUCCCUUCUACAGUA (Evi#1)       (SEQ ID NO: 2)

UAACGGAAGGCCAUUGGAA (Evi#2)       (SEQ ID NO: 3)

UAAAGGAUAUCCGGUUGGUU (Evi#3)      (SEQ ID NO: 4)

Pool of GCUGAAACAUGCAGUUGUA,      (SEQ ID NO: 5)

GAUAAAGGCUACUGUUGGA,              (SEQ ID NO: 6)

CCACUAAUGUCCAGCGUUU.              (SEQ ID NO: 7)

ACAAGUAGCUGAUAUUGAU (β-catenin),  (SEQ ID NO: 8)

P002070-01-20 (con).
```

Cells were transfected in 384-, 24- or 6-well plates using 20 nM siRNA. SiRNA transfected cells were cultured for 3 days prior to use for immunocytochemistry, Western blot and qPCR experiments.

For xenografted subcutaneous tumor experiments, 3×10$^6$ U87 MG cells in 0.1 ml PBS were injected into the flanks of 6-8 weeks old Nod/SCID mice. tumor growth was monitored by caliper measurement of for 4 weeks. tumor growth was calculated according to the following formula: 0.5 length× width$^2$. All animal experiments were approved by the local authorities (Regierungspräsidium Karlsruhe, Germany, 35-9185.81/G-S2/10).

Cell Proliferation, Colony Forming Assay and Transwell Migration Assay

To assess cell viability, 500 cells were plated in quadruplicates in 384-well plates and viability was measured at different time points using CellTiter-Glo (Promega) according to the manufacturer's protocol.

Colony forming assay was performed with U251 cells. Cells were transfected with siRNA. After two days 1000 cells per 6-well were plated in triplicates and incubated for 2 weeks before they were stained with 0.1% cristal violet. Colonies with more than 50 cells were counted. For migration assays, invasion chambers (Coming) were used according to the manufacturer's instructions. Briefly, uncoated Transwell membrane filter inserts (6.5 mm in diameter 8-µm pore size, 10-mm-thick polycarbonate membrane) were placed in a 24-well tissue culture plates. Cells (1×10$^5$) suspended in DMEM containing 10% serum were pipetted in duplicate into the top chambers and DMEM containing 10% FBS was added to each bottom chamber. After 18 h incubation at 37° C., non migrating cells were removed from the upper face of the filter using cotton swabs and cells on the lower filter surface were fixed and stained with hematoxylin (Sigma) The number of cells per microscopic field was counted light microscopically. The average number of migrating cells within 7 random fields was calculated.

Western Blotting

Cell pellets were dissolved in lysis buffer containing 8 M Urea, 0.1 M NaH$_2$PO$_4$10 mM TrisHCL, Lysates were incubated on ice for 10 min. And the centrifuged at maximum speed for 20 min. The supernatants were collected and protein concentrations were determined by BCA method. Protein (10-30 µg) was separated on 4-12% NuPage gradient gels and transferred to PVDF-membranes. Membranes were blocked and incubated overnight at 4° C. or 1 h at RT with one of the following antibodies: anti-Gpr177 (1:500, DKFZ Heidelberg), anti-β-catenin (1:2000, BD Transduction Laboratories #610154). Blots were then incubated with corresponding horseradish peroxidase-conjugated secondary antibodies (1:10.000, Sigma). The antiserum (???) against Gpr177 was generated against the peptide FTSPKTPEHEGRYYNC (SEQ ID NO:1) of the first extracellular loop.

Immunohistochemistry and Cytochemistry

Normal brain samples were obtained from autopsy cases and human tumor tissues from bioptic samples from the department for Neuropathology, Institute for Pathology university of Heidelberg. All samples were analysed in an anonymized manner as approved by the local institutional ethics boards. At least 3 samples were analysed per tumor grade.

Immunohistochemical studies were performed on formalin-fixed, paraffin-embedded specimen. Briefly, sections were deparaffimized in xylene and passed through graded alcohols and further rehydrated in phosphate buffered saline (PBS). Antigen unmasking was carried out by microwaving the sections for 10 min. In 10 mM citrate buffer (pH 6.0) Sections were then treated with 1% H$_2$O$_2$ for 30 min. To block endogenous peroxidase followed by incubation with Avidin/Biotin blocking solution (Vector) for 1 h at RT in a humid chamber. The sections were then incubated overnight at 4° C. with primary antibodies against Gpr177 (1:200, DKFZ Heidelberg). Peroxidase-conjugated secondary antibody (1:2000 DAKO) was used for 1 h incubation time at RT followed by 30 min. incubation with AB-complex. Diaminobenzidine (DAB) in buffer was used until sections developed color. Sections were then counterstained using hematoxylin. Negative control experiments included omission of the primary antibody. For immunocytochemistry, siRNA transfected U87MG cells were fixed in 4% PFA for 10 min. at RT. After washing steps, blocking was done with 1% BSA-PBS for 30 min. The primary antibody (1:200, DKFZ Heidelberg) against Gpr177 was incubated overnight at 4° C. Fluorescein isothiocyanate (FITC)-labeled secondary antibody (1:800) was added for 1 h at RT, Nuclei were counterstained with Hoechst dye. Images were taken with a ZEISS LSM 510 META Confocal Microscope at 63× magnification.

Flow Cytometry

Lentivirally shRNA transduced U87MG and NCH42ik cells were cultured for 16 h (U87MG, 20% confluence) or 7 days (NCH42Ik) prior to analysis. Cells were harvested and stained with 200 μg/ml propidium iodide, 0.1% NaAzide and 0.1% Triton, 10 μg/ml RNAses for 3 h. A total of 20.000 nuclei were examined by FACS Array (BD Bioscience).

Real Time Transcription (RT)-PCR Analysis

Total RNA was extracted using Rnaesy extraction kit (Qiagen) according to the manufacturer's instructions. Reverse transcription and quantitative PCR was performed with 25 ng cDNA and LightCycler 480 Probes Master as described (Roche). Relative mRNA expression was calculated as a fold-change versus control. Primers were as follows:

```
Evi/Gpt177:F:TCATGGTATTTCAGGTGTTTCG              (SEQ ID NO: 9)

R: GCATGAGGAACTTGAACCTAAAA (probe#38, Roche);   (SEQ ID NO: 10)

β-Catenin: P.AGCTAGACCAGCTCTCTCTTCA,             (SEQ ID NO: 11)

R: CAATATCAAGTCCAAGATCAGC (probe #21, Roche),   (SEQ ID NO: 12)

: Cyclin DI: F: GAAGATCGTCGCCACCTG,              (SEQ ID NO: 13)

R: GACCTCCTCCTCGCACTTCT (probe #67, Roche);     (SEQ ID NO: 14)

c-Myc:F: CACCAGCAGCGACTCTGA,                     (SEQ ID NO: 15)

R: GATCCAGACTCTGACCTTTTGC (probe #34, Roche);    (SEQ ID NO: 16)

PTMA: F: CCTGCTAACGGGGAATGTAA,                   (SEQ ID NO: 17)

R: CTTCCTCTTCTTCGTCTACCTCA (probe #75, Roche);  (SEQ ID NO: 18)

IL-8: F: ATGGTTCCTTCCGGTGGT                      (SEQ ID NO: 19)

R: AGACAGCAGAGCACACAAGC (probe #72, Roche)       (SEQ ID NO: 20)
```

Expression Profile of Glioma Samples

RNA expression of Gpr177 in normal brain and tumor samples relative to human reference RNA (Stratagene, La Jolla, USA) was determined using micoroarray analysis as described (Tödt et al., 2010).

Expression Profiling of Gpr177 Silencing Experiments

RNA was extracted from two biological replicates of cells transfected with either w Gpr177 siRNA#1, Gpr177 siRNA#3 or con The poly(A)+ fraction was isolated from each of the six samples and used to probe an Illumina HumanHT-12 v4 beadchip. These arrays have on average 15 beads per probe, and cover more than 47,000 transcripts and known splice variants. The complete data set contained 6 samples ($R^2$ of all normalized replicates was >0.98).

Using BeadStudio software (v3.2+), summary intensities for each bead type on the array were produced, and quantile normalization between samples was performed. The limma package (v 3.2.1), part of the Bioconductor package suite, was employed to test for differential expression. This test assumes a linear model for gene expression levels. The differential expression test between both Gpr177 and control samples is based on the null hypothesis that the expression values of a gene in the samples come from the same distribution, and results in p-values for each gene and sample pair. Specifically, a simple design matrix was formed to fit a linear model to each gene expression value, where the coefficients corresponded to the RNA sources of interest (i.e. Gpr177 siRNA#1, Gpr177 siRNA#2 and con siRNA). Contrast of interest extracted from the fit where: 1) Genes which respond to knockdown using Gpr177 siRNA#1; 2) Genes which respond to knockdown using Gpr177 siRNA#3; 3) Genes which respond similarly in both the knockdowns using Gpr177 siRNA#1 and Gpr177 siRNA#3. Data from the latter contrast is presented in this study. An empirical Bayes method was used to moderate standard errors and estimate log fold-change from the data, and a moderated t-statistic was used to assess differential expression. Genes which had an adjusted (Benjamini-Hochberg) p-value<0.01 with respect to the third contrast listed above were regarded as differentially expressed, and used for further KEGG pathway analysis. Bioconductor GOStats (v2.14), Category (v2.12) and KEGG.db (v2.14) packages where used to perform a Fisher's exact test KEGG categories for over-representation in this gene set.

Statistical Analysis

Unless otherwise indicated, data are expressed as mean±SD. Statistical significance was calculated by 2-tailed Student's 7-T-test with unequal variance. A p-value of less than 0.05 was considered statistically significant and marked by asteriks. Two asterisks represent p-values of less than 0.01.

Results

Evi/Wls is Overexpressed in Astrocytomas

Gpr177 is ubiquitously expressed during mouse embryonic development with particular prominent expression in the developing head structures. Expression persists also in adult tissues {our unpublished data}. Similar to *Drosophila*, previous studies showed that Gpr177 is essential for Wnt-dependent developmental processes, indicating that Gpr177 might also contribute to Wnt-dependent adult tissue homeostasis and pathophysiology. To assess Gpr177 expression during brain tumorigenesis, we used an expression profile database of 71 different graded astrocytic tumor samples (grade II: n=8; grade III: n=11; grade IV [primary: n=42 and secondary: n=10]).

Strikingly, we found that Gpr177 was strongly overexpressed in low and high grade brain tumors as compared to control tissues (FIG. 1A), while no significant differences were observed between low grade and high grade tumors. These findings were confirmed in an independent data set from the Molecular Brain Neoplasia Database (REMBRANDT) (ref PMID: 19208739) which revealed a significantly upregulated Gpr177 expression in glioma. Moreover, high levels of Gpr177 expression are associated with poor overall survival of glioma patients (p=0.013) (FIG. 7). Gpr177 expression showed no association with gender, age, p53 mutation status, IDH mutation status, and MGMT methylation status (data not shown).

Figure 1B:
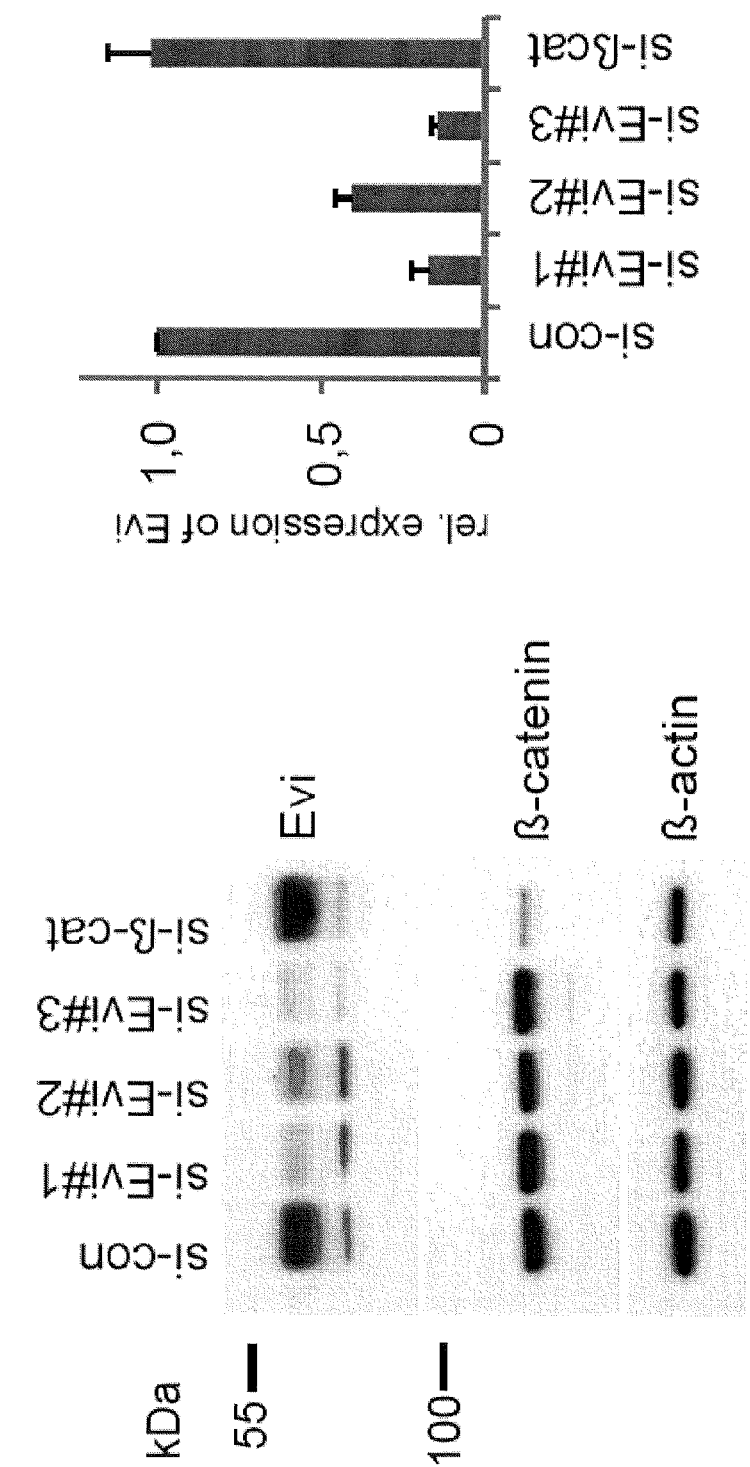
Figure 8A:
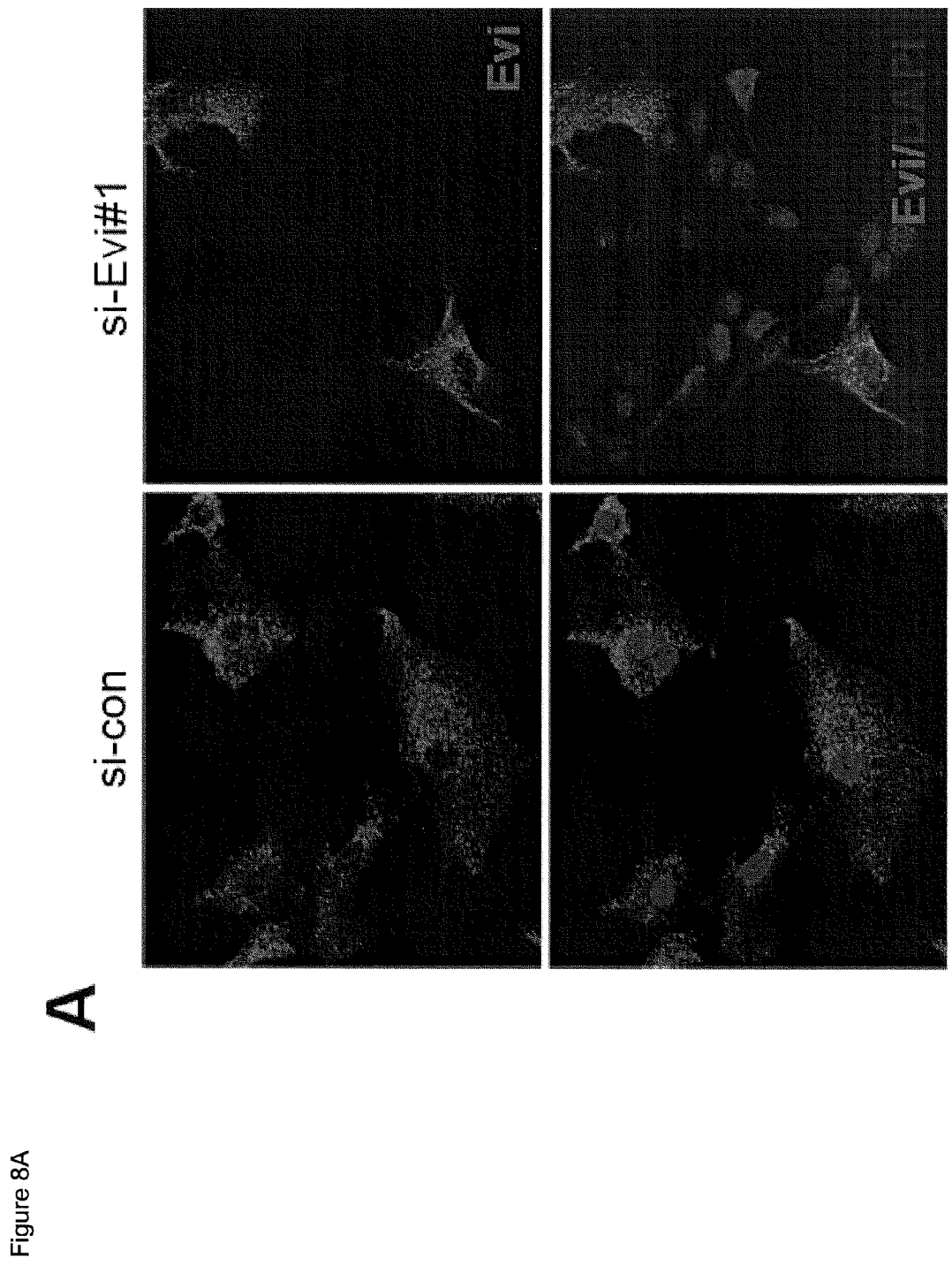
Figure 8B:
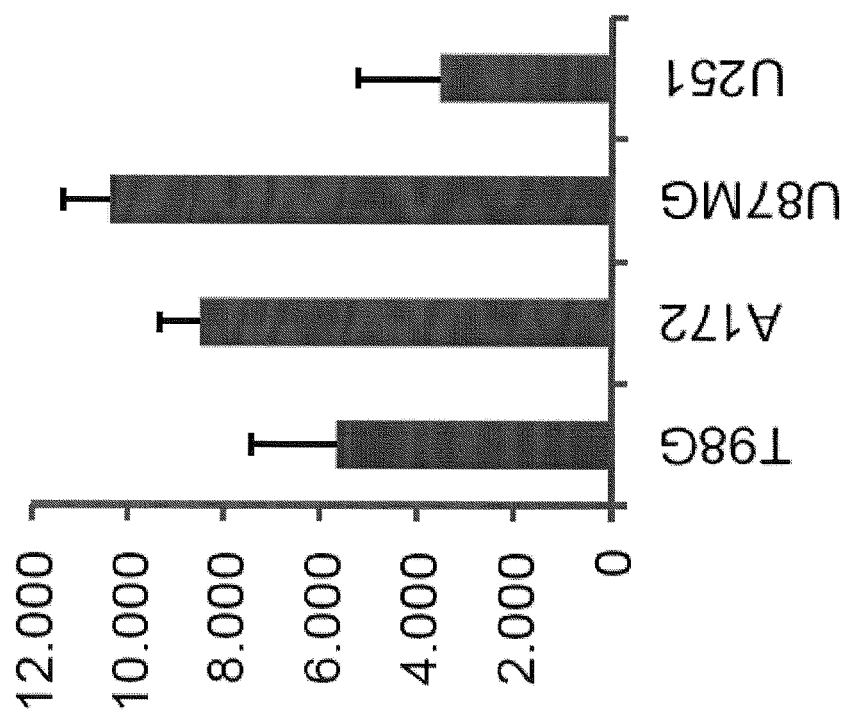

In order to examine the expression of Gpr177 protein, we raised an antibody against the N-terminus. We showed that the antibody recognizes a protein with the expected size of ~45 kDa which is lost after depletion by Gpr177 specific siRNAs (FIG. 1B). Immunofluorescence staining showed that Gpr177 protein is detectable in U87MG cells with intense perinuclear staining (FIG. 8A). Gpr177 protein levels were then examined in astrocytic tumors tissue (FIG. 1C-F). Consistent with the mRNA expression data, Gpr177 protein was highly expressed in tumor cells of both low and high grade glioma (FIG. 1C-F). Moreover, our histochemical data revealed that Gpr177 was restricted to perivascular smooth muscle cells, ependymal cells, few neurons and astrocytes in normal brain tissue. Taken together, we describe Gpr177 as a protein strongly overexpressed in low and high-grade glioma by multiple independent methods.

Silencing of Gpr177 Leads to Downregulation of Pro-proliferative Genes and Interleukins in Glioma Cells In order to analyze the functional role of Gpr177 in glioma, we performed experiments with glioblastoma cell lines and glioblastoma-derived cancer stem-like cells. Different glioblastoma cell lines express Gpr177 in comparable amounts as shown by qPCR analysis of U87MG, A172, T98G and U251 cells. Among these cell lines U87MG cells shows highest Gpr177 expression (FIG. 8B) and we focused our loss-of-function analysis to this cell line.

Figure 2A:
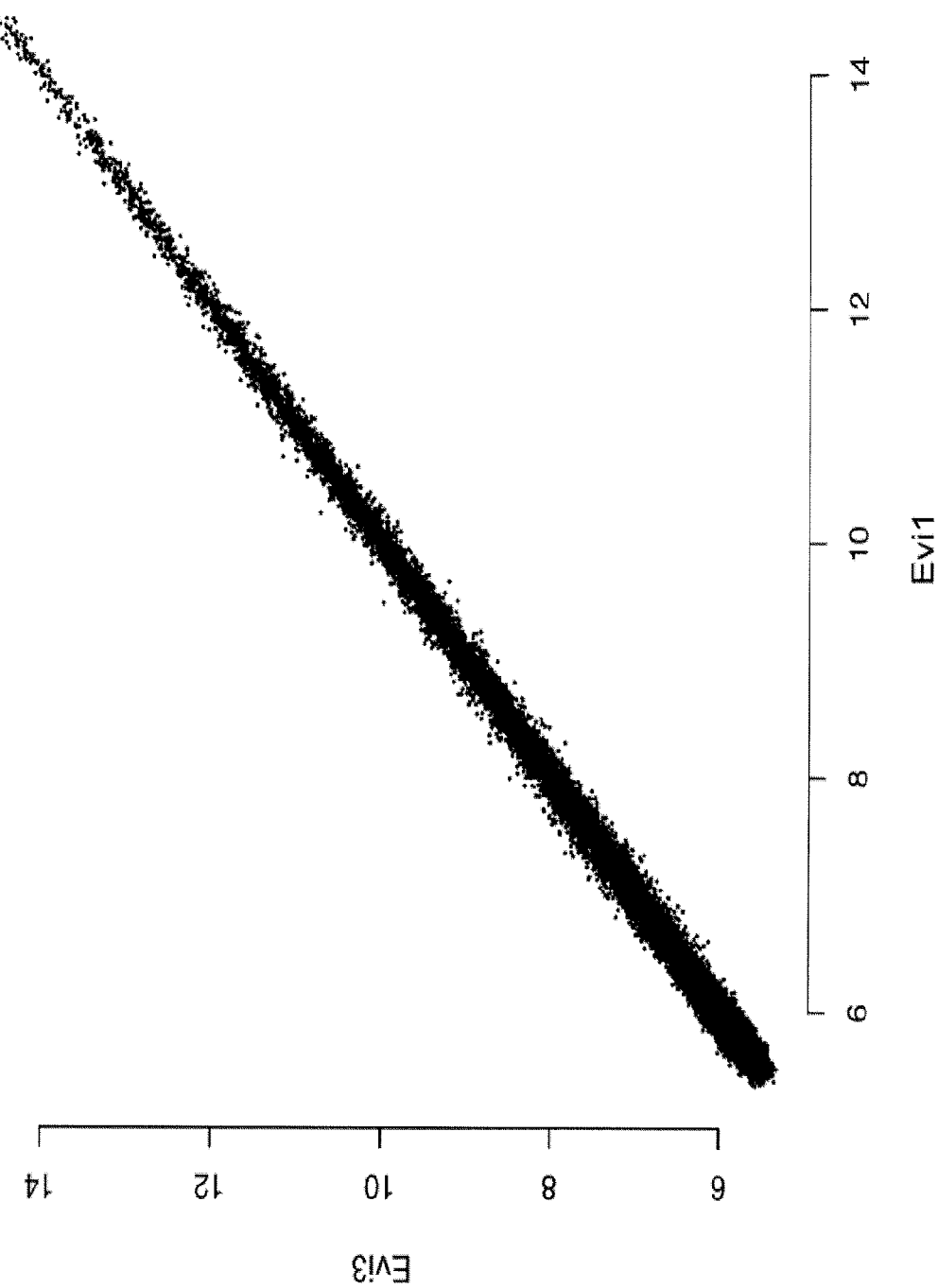
Figure 2B:
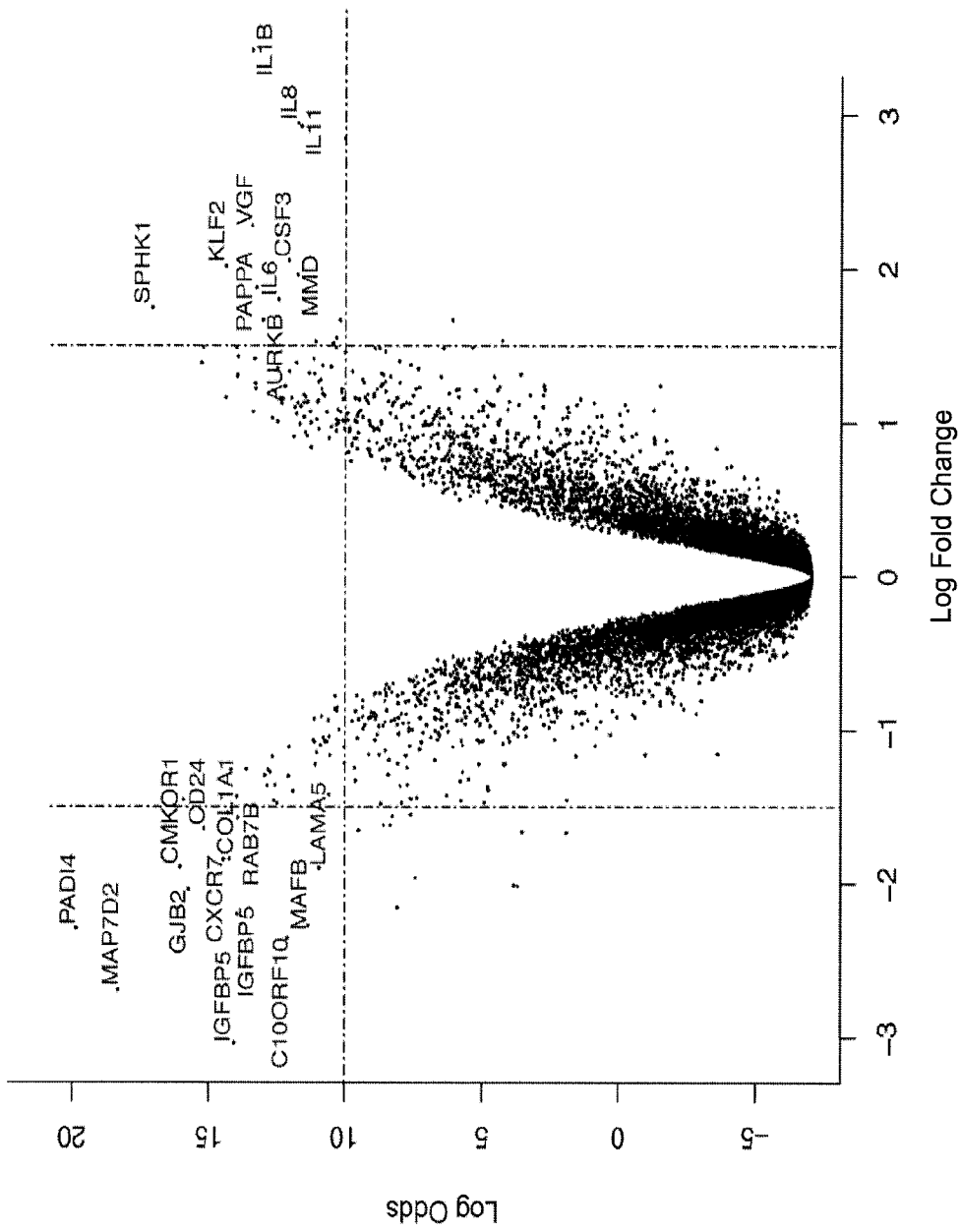

To identify genes that are controlled by Evi, we compared expression profiles of glioma cells after transfection with Gpr177 and control siRNAs. Expression values after silencing of Gpr177 with two independent siRNAs (siRNA#1, siRNA#3) showed that both siRNAs affected the transcription profile similarly ($R^2=0.99$), with no obvious off target effects (FIG. 2A). We used linear modeling of gene expression to analyze expressed genes in both siRNAs compared to control. From this analysis, we identified 139 genes that were significantly differentially expressed with a log odds ratio>10, of which 30 also had a logfold change 1.5 (FIG. 2B).

Figure 2C:
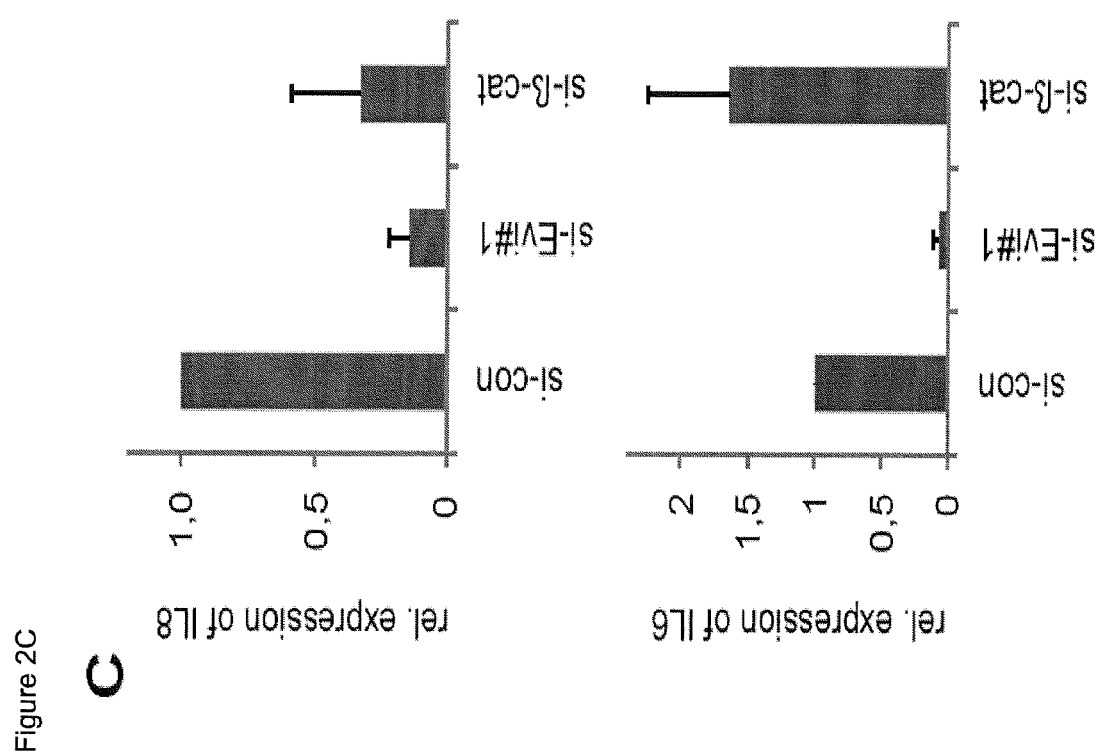

Interestingly, we found that members of the interleukin family including IL-8, IL-6, IL-1B, IL-11 were strongly downregulated after Gpr177 depletion (FIG. 2C). High levels of IL-6 and IL-8 have been linked to tumor generation and poor prognosis in many cancer types, including glioblastoma, however, little is known how they are controlled and how they contribute to glioblastoma formation or progression.

We then classified differentially expressed transcripts by KEGG category.

This analysis showed that Gpr177 depletion strongly affected the expression of genes involved in cell cycle regulation, DNA replication, mismatch repair and nucleotide excision repair, among others (FIG. 9). Quantitative RT-PCR confirmed the regulation of c-Myc, Cyclin D1, PTMA and Tenascin-C by Gpr177 (FIG. 3). Since loss-of Gpr177 can affect the production of both canonical and non-canonical Wnt pathways, we also tested whether these genes were downregulated after knock-down of β-catenin, which is only required for canonical Wnt signaling. As shown in FIG. 3, β-catenin silencing only influences PTMA expression, showing that the compendium of Gpr177 target genes in glioma consists of genes controlled by both canonical and non-canonical Wnt signaling.

Gpr177 is Required for Glioma Cell Proliferation

Based on the observed transcriptional changes of cell cycle regulators, we next examined the consequences of Gpr177 silencing on cell proliferation of U87MG, A172, and T98G cells. Depletion of Gpr177 or β-catenin by RNAi resulted in significant inhibition of glioma cell proliferation of U87MG and A172 compared to control glioma cells (FIGS. 4A and B, FIG. 11), while T98G cells revealed no change in proliferation after Gpr177 silencing. Interestingly, Evi-dependent U87MG and A172 cells are PTEN mutant and p53 wild-type, whereas the non-dependent T98G cell line harbors PTEN wild-type and p53 mutant alleles (Table 1, http://www.sanger.ac.uk/genetics/CGP/CellLines/).

TABLE 1

Mutation status of glioblastoma cell lines

| | P53 | PTEN |
| --- | --- | --- |
| U87MG | wildtype | mutant |
| A172 | wildtype | mutant |
| T98G | mutant | wildtype |
| U251 | mutant | wildtype |
| LN229 | wildtype | wildtype |
| LN18 | mutant | wildtype |

Figures 11A, 11B:
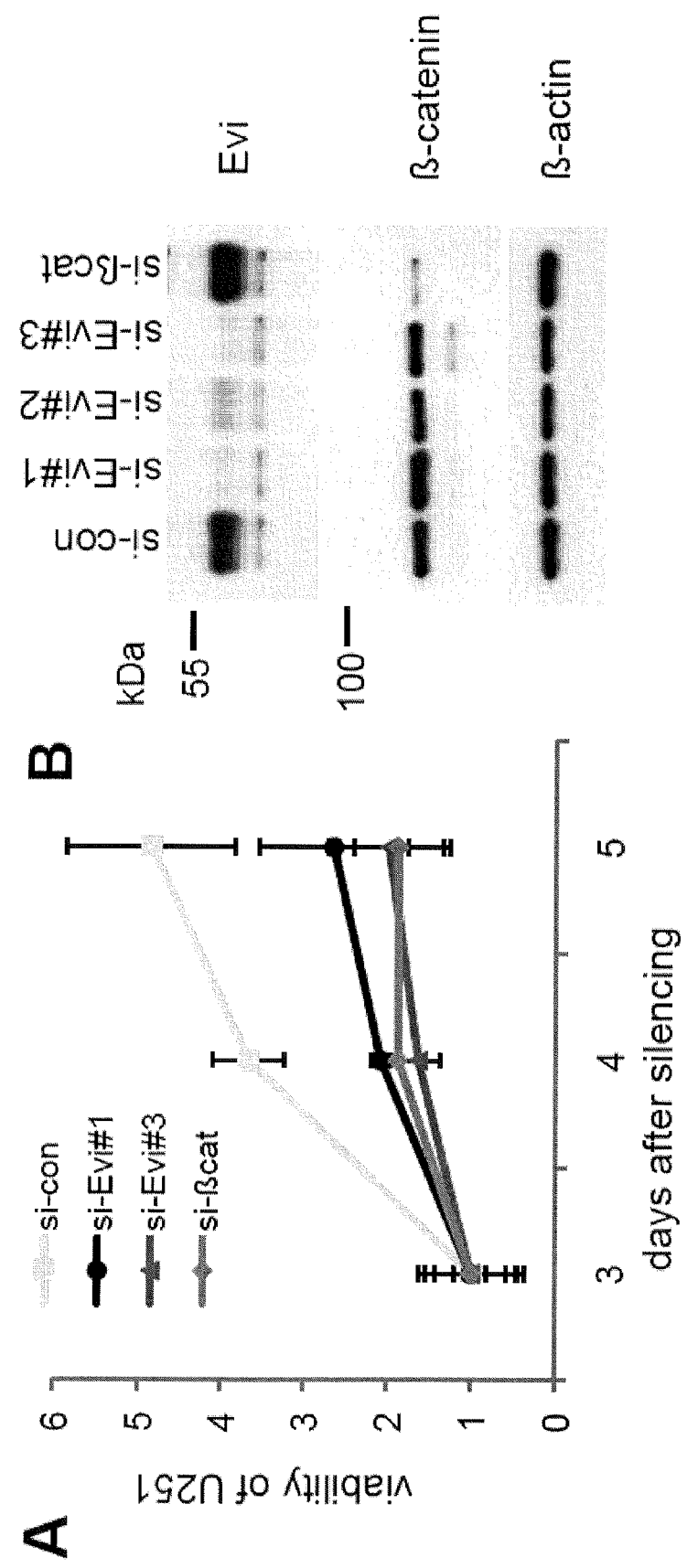
Figure 11C:
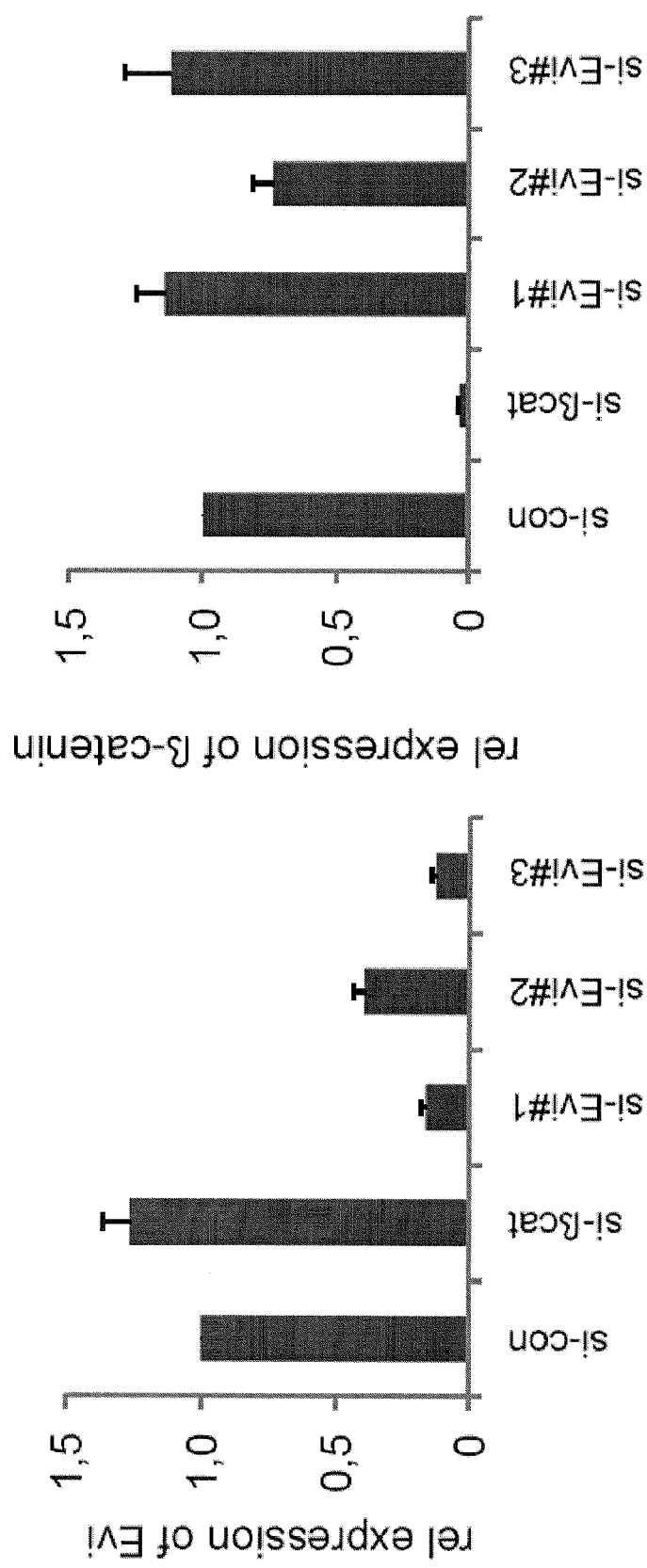
Figure 11D:
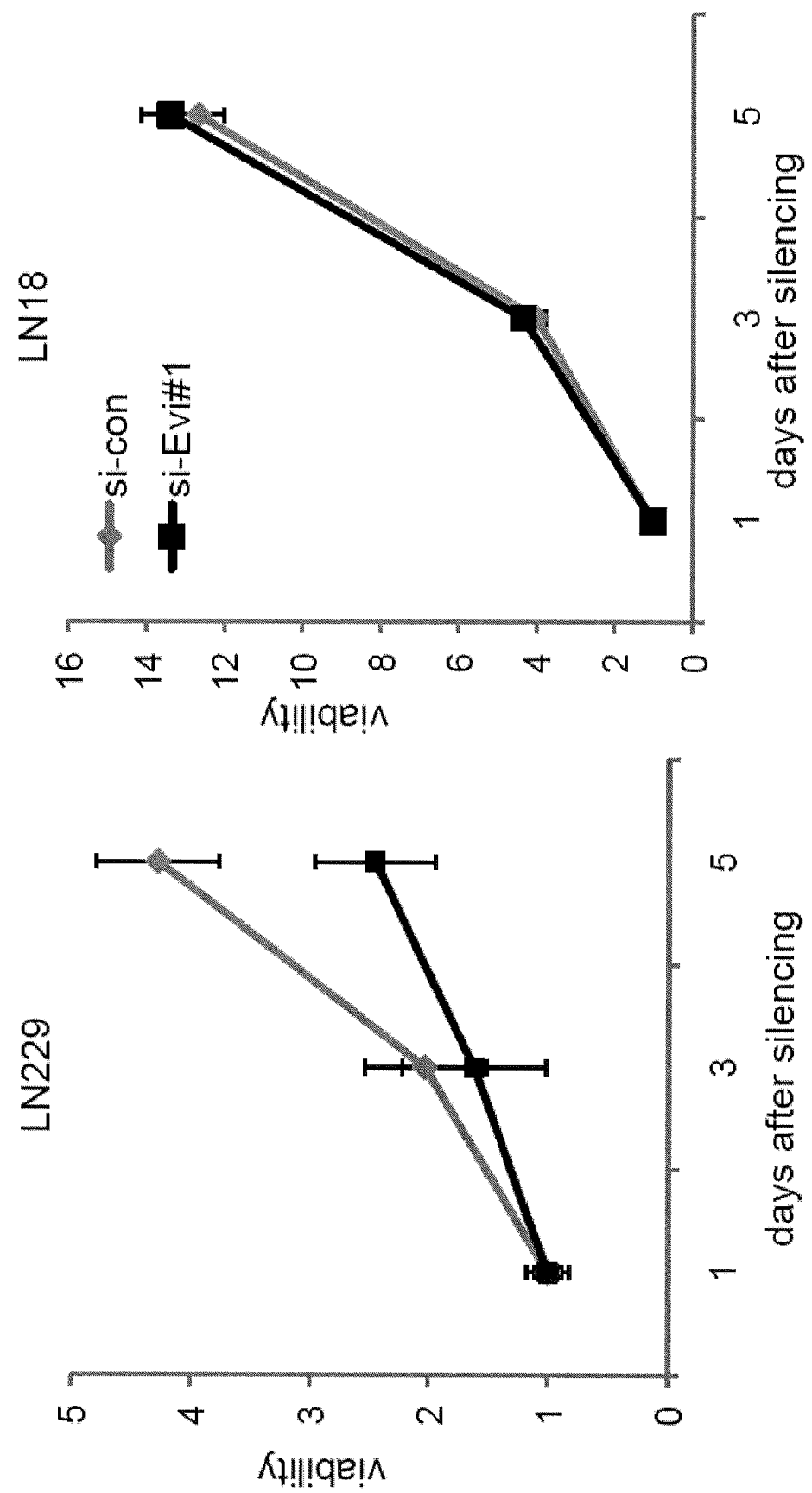
Figure 11E:
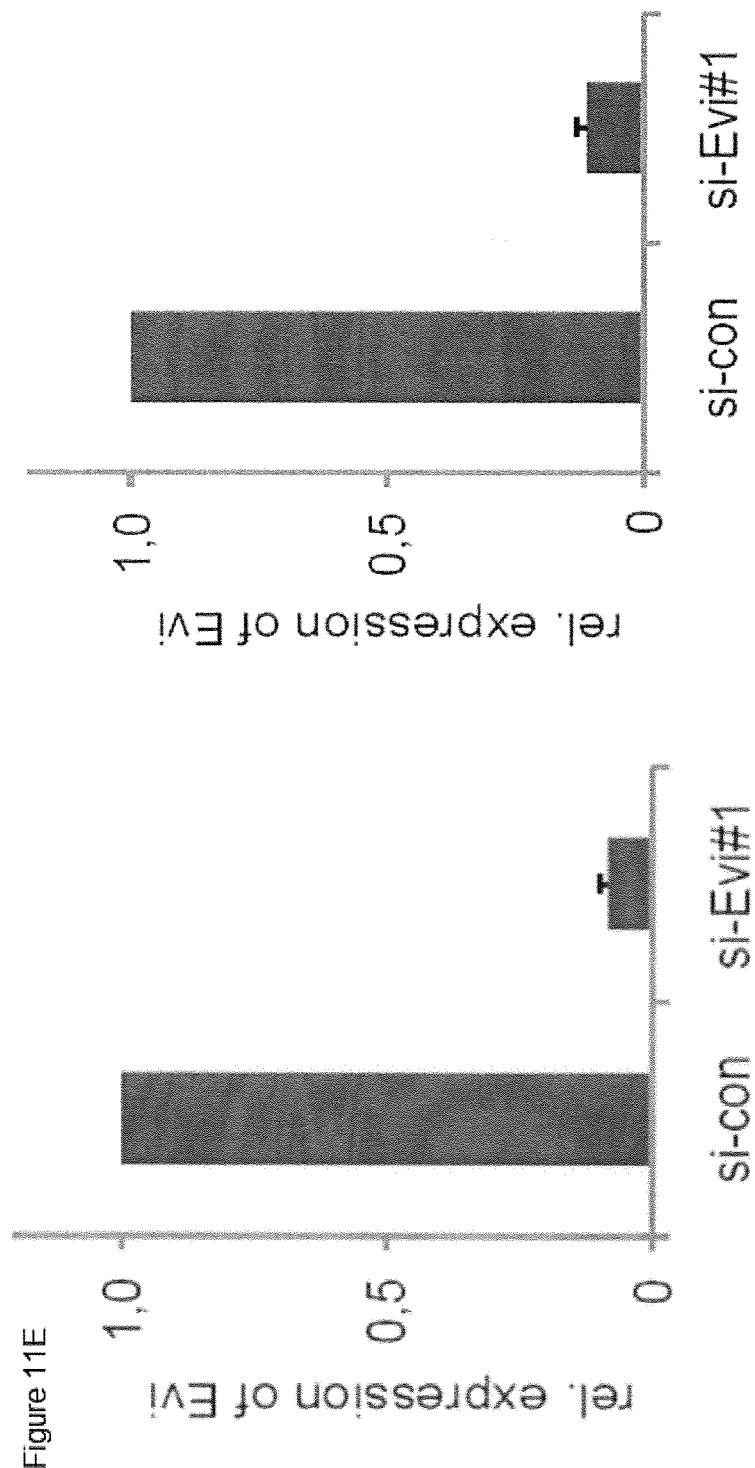

The dependency on mutational status was confirmed in LN18 cells, which are PTEN wild-type and p53 mutant. LN18 also do not show a significant growth arrest LN18 (FIG. 11D). Moreover, glioblastoma cell lines with alternative combinations of PTEN and p53 alleles such as U251 (PTEN mutant, p53 mutant) and LN229 (PTEN wildtype, p53 wild-type) showed a decrease in proliferation after Gpr177 silencing (FIG. 11). Taken together, we show that depleting Evi, and thereby the secretion of Wnt ligands, significantly reduced the proliferation of glioma cells except in cell lines with p53 mutation and wildtype PTEN.

Figure 4A:
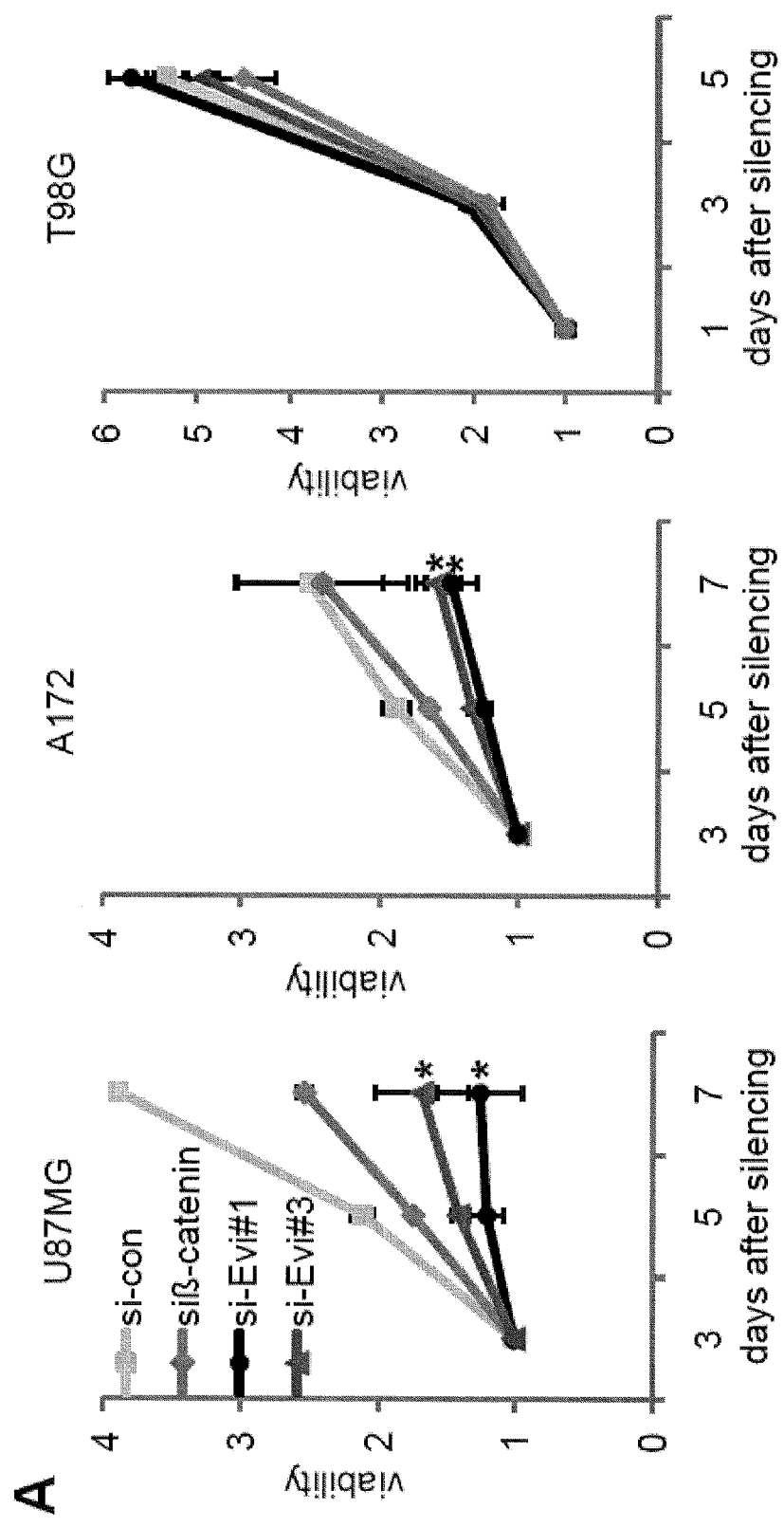
Figure 4B:
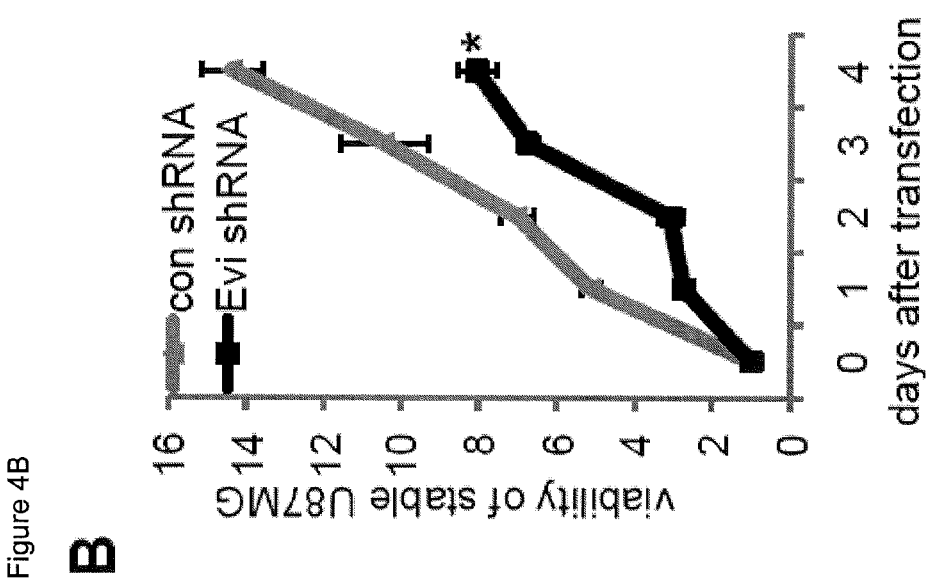
Figure 4C:
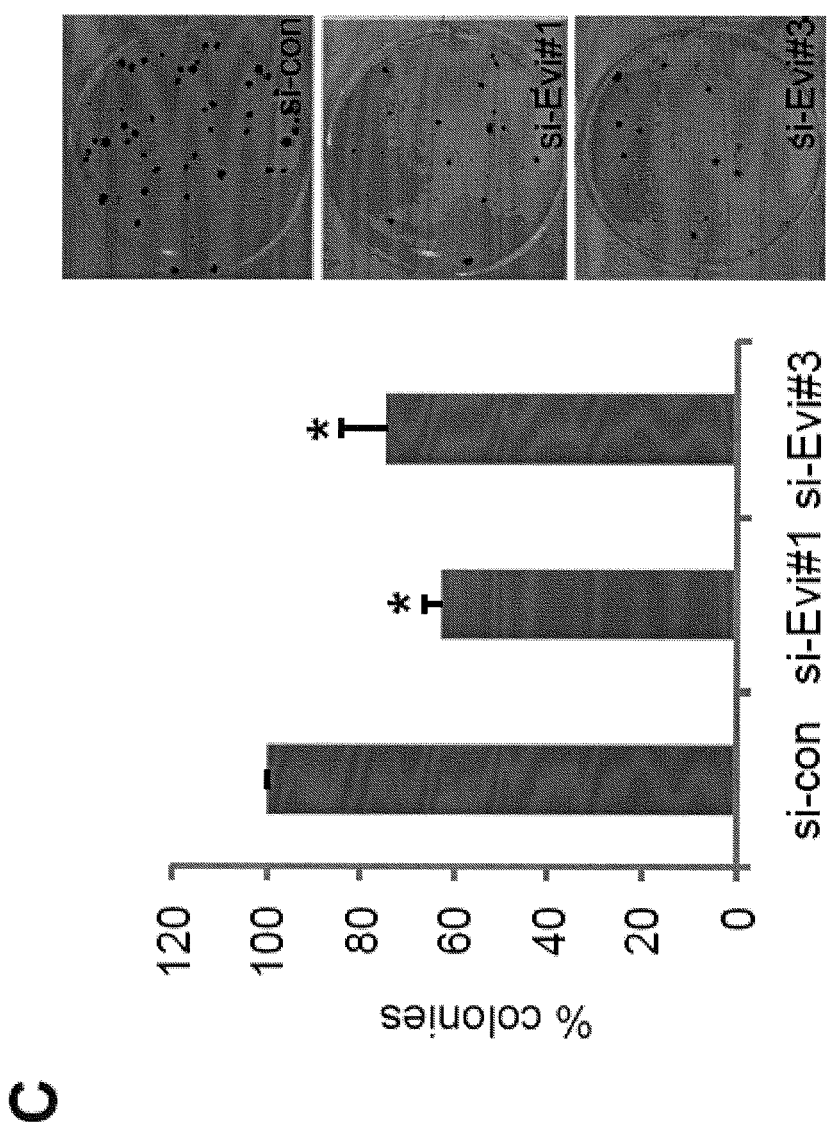
Figure 4D:
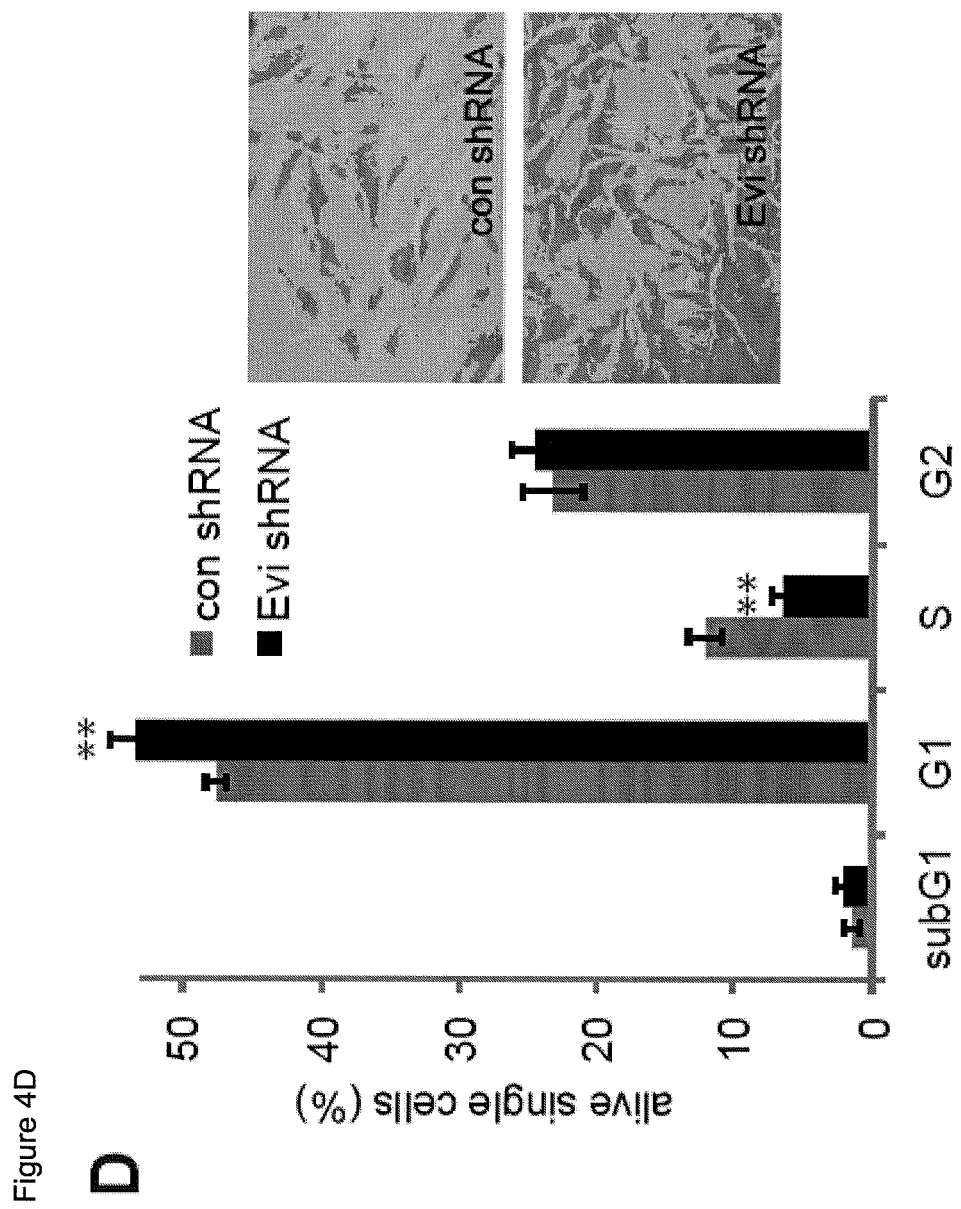

These short term proliferation experiments were extended by lentiviral shRNA-based Gpr177 silencing which facilitated Gpr177 silencing for prolonged periods of time. Long term shRNA-based silencing of Gpr177 expression similarly led to reduced U87MG cell proliferation as observed in the siRNA-based experiments (FIG. 4B). To provide additional evidence that Gpr177 silencing affects cell survival, we performed a colony formation assay with U251 cells. Downregulation of Gpr177 led to significantly less colonies compared to control transfected cells (FIGS. 4C and 11). The negative effect of Gpr177 silencing on glioma cell proliferation was further analyzed by flow cytometric assessment of cell cycle distribution. Gpr177 depletion in U87MG cells led to a G1 arrest as shown by significantly increased number of cells in G1-phase in Evi-silenced cells compared to control shRNA-silenced cells (53.4% vs. 47.6%) (FIG. 4D). Concomitantly, the number of cells in S-phase was reduced in Gpr177 silenced cells (6.5% vs. 12.1%). In contrast to this the subG1-fraction of cells is not significantly changed indicating that the observed decrease in cell proliferation is due to less viability but not increased apoptosis. Gpr177 depletion also led to distinct cell shape. In particular the cells are more compacted compared to the elongated control U87MG cells (FIG. 4D). Thus, our results demonstrate that Gpr177 is required for cell viability and cell proliferation of glioblastoma cells.

Gpr177 Silencing Induces Apoptosis in Glioma Stem-like Cells

Figure 5A:
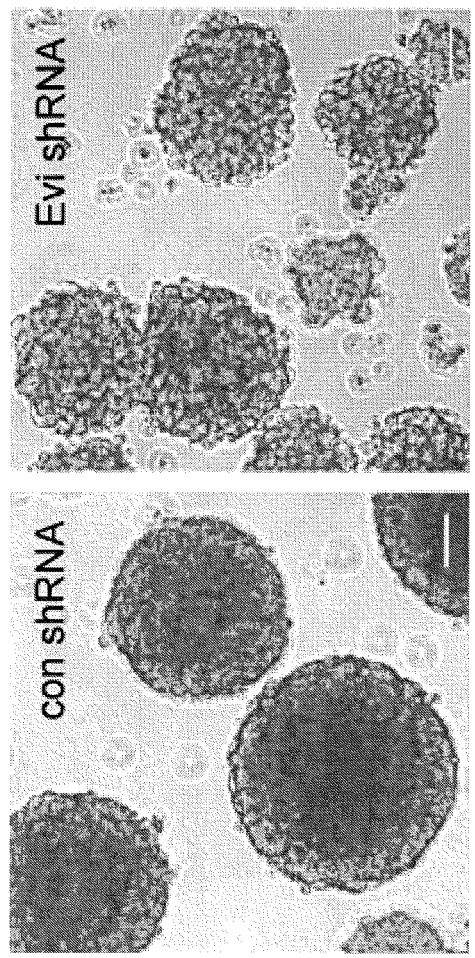

We next analyzed whether Gpr177 is required for proliferation and survival in glioma stem-like cells. Previous studies have shown that spheroid forming cells isolated from human glioblastoma and cultured under serum-free conditions are enriched for glioma cancer stem cells. These cells comprise a subpopulation of glioma tumor cells that are capable of differentiating into an actively expanding tumor bulk. Microscopic view of spheres transduced with Gpr177 shRNA and scrambled shRNA showed changes in their appearance. Gpr177 silenced spheres are smaller and lost their packed condensed morphology compared to control spheres (FIG. 5A). Further analysis of apoptotic cells after Gpr177 shRNA transduction revealed an increase in apoptosis as demonstrated by a significant rise in the sub-G1 fraction (FIG. 5B). In addition, the amount of viable cells was significantly reduced in Gpr177 depleted spheroid cultures (FIGS. 5C and D). These experiments demonstrate that Gpr177 is required for cell survival and proliferation in primary patient-derived glioblastoma cells.

Effect of Gpr177 shRNA in U87MG on Tumor Cell Migration and Tumor Growth

Glioblastoma are characterized by pronounced invasion of tumor cells into the surrounding healthy tissue. Therefore we performed transwell migration experiments to examine the consequences of Gpr177 depletion in glioma cells on cell migration. As shown in FIG. 6A, siRNA-based silencing of Gpr177 expression caused a 32% inhibition of migration of glioma cells, whereas a more robust lentiviral shRNA-induced downregulation of Gpr177 caused a 63% decrease in migratory behavior.

Figure 6B:
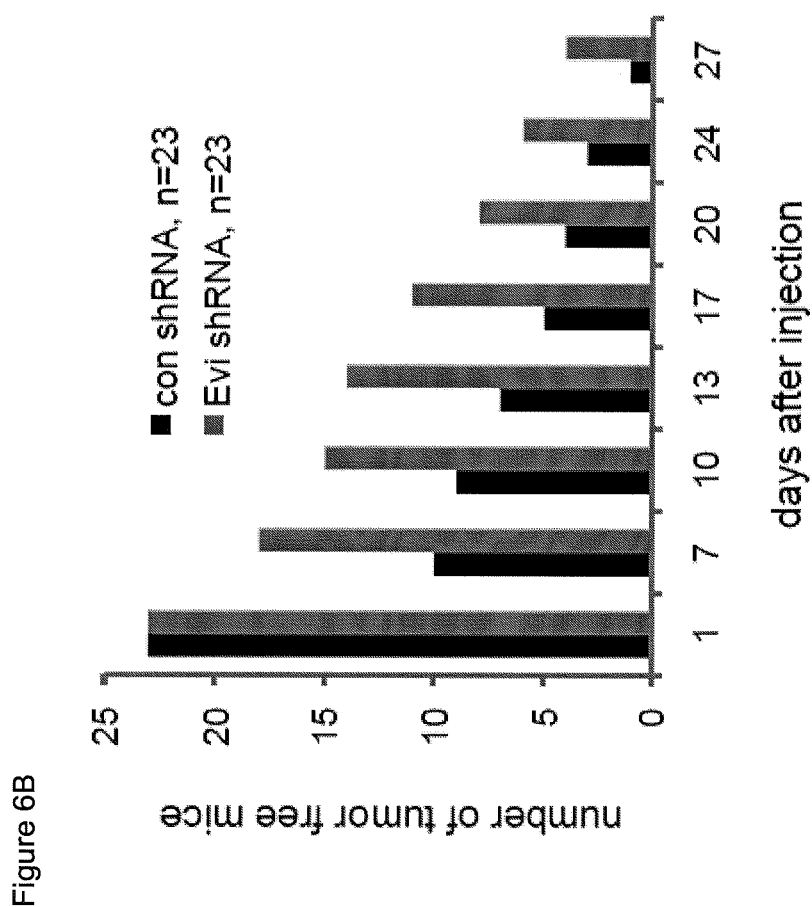

The effect of Gpr177 silencing on glioma tumorigenesis in vivo was examined by comparatively studying the growth of subcutaneously grafted control and Gpr177 shRNA transduced U87MG tumors. Corresponding to the reduced proliferative and migratory capacity of Gpr177 silenced U87MG cells in culture, shRNA-based downregulation of Gpr177 caused a significant reduction of glioma tumorigenesis (FIG. 6B). Silencing of Gpr177 induced a delay in the onset of tumors growth indicating that depletion of Gpr177 affects growth and survival of glioblastoma cells after xenotransplantation. Our experiments showed that Gpr177 interferes with tumor-promoting characteristics like tumor cell migration and tumor initiation.

Discussion

Despite recent advances in surgery and adjuvant therapy, the prognosis of overall survival for patients with malignant brain tumors remains poor. This emphasizes the need for in-depth understanding of the molecular pathogenesis and the development of new concepts for cancer therapy. Aberrant activation of Wnt signaling represents a crucial driving force in a variety of human cancers. Here we want to point out the contribution of Wnt signaling in brain tumor formation.

The present study was aimed at characterizing Evi, which represents so far the most upstream component of the Wnt signaling pathway that has been analyzed concerning tumor development. Previously, Gpr177 was identified in a genetic screen in *Drosophila* as an essential and specific component in the Wnt producing cell. In mammals, it has been shown that Gpr177 binds to and is required for the release of Wnt1, Wnt3 and Wnt5a. Since it is a single gene in vertebrates as well as in invertebrates, it is likely that Gpr177 is involved in the secretion of all Wnt proteins affecting both canonical and non-canonical Wnt ligands. These properties make Gpr177 an interesting target for modulating aberrant Wnt signaling at the source of production.

Figure 8C:
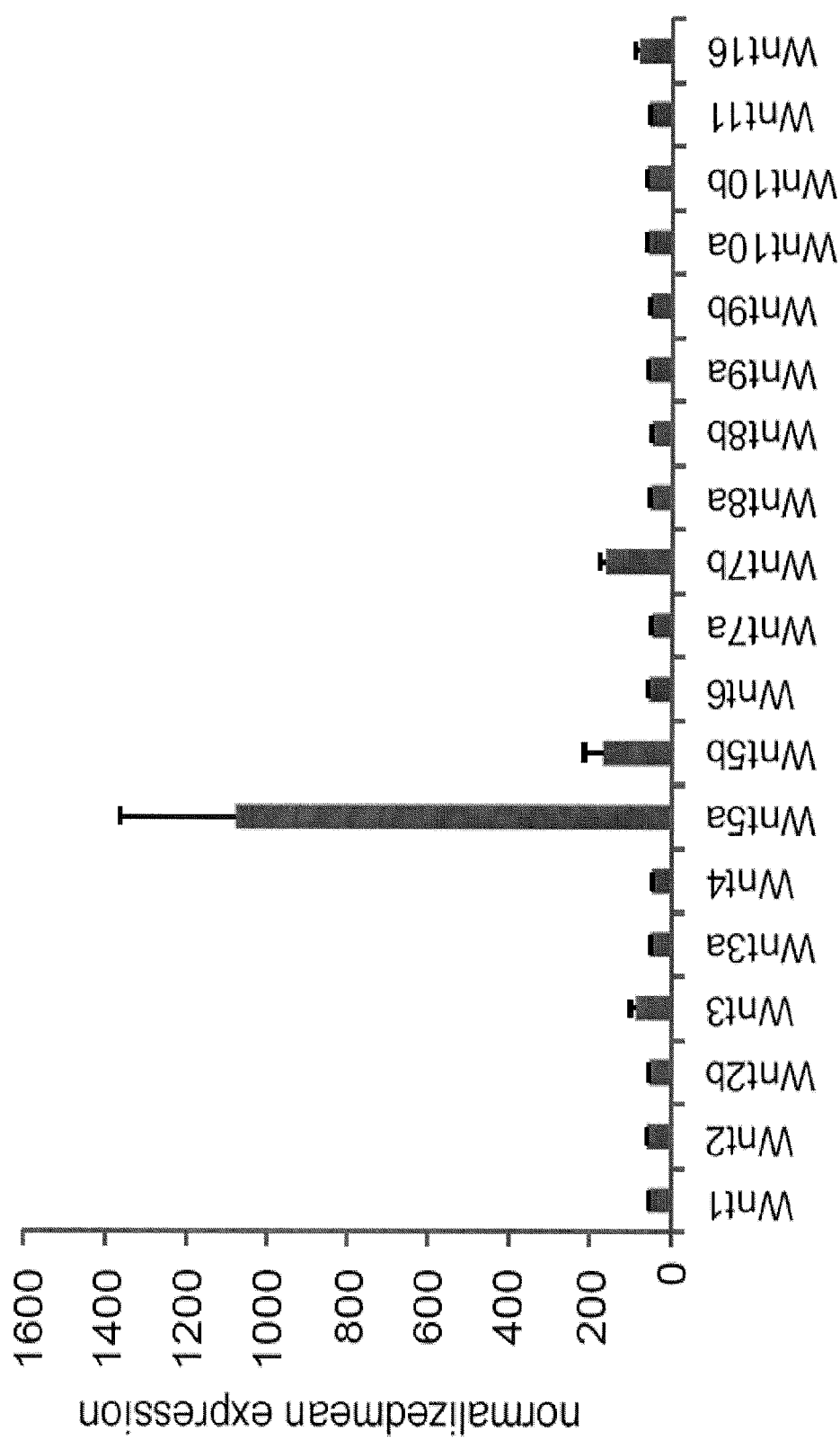

We found that Gpr177 expression is upregulated in glioma patients of different grades when compared to normal brain tissue. In astrocytoma grade II, Gpr177 expression is strongly increased and remains at high levels in astrocytoma grade III and IV, indicating that highlevels of Gpr177 might already be required for early neoplastic transformation. The data might also imply that the production of Wnt ligands exceeds the capacity that is found in normal brain tissue, and is required for both tumor initiation and tumor growth. This is supported by previous studies that showed upregulation of both canonical and non-canonical Wnt signaling components including Wnt1, Wnt2 and Wnt5a. Non-canonical Wnt5a is the most abundant Wnt ligand in glioblastoma cell lines such as U87MG (FIG. 8C). Previous results showed that Wnt5a has oncogenic and antioncogenic properties depending on the cell type of the tumor. Colorectal cancer is an example where Wnt5a has tumor suppressive function. For brain tumors it has been reported that Wnt5a stimulates cell motility and infiltrative activity of tumor cells. Moreover, Wnt5a expression correlates with brain malignancy.

In vitro experiments revealed that down regulation of Gpr177 in different glioblastoma cell lines and glioblastoma derived cancer stem-like cultures affects cell proliferation, migration and apoptotic cell death. The effect of Gpr177 on glioblastoma cell survival was further confirmed by the observation of reduced tumorigenesis in nude mice after xenotransplantation of Gpr177 shRNA transduced cells. Furthermore, the restricted cell proliferation after Gpr177 silencing in glioblastoma cell lines was accompanied by cell cycle arrest in G1.

Genetic profiling of glioma identified characteristic alterations. Loss-of-function mutations of the phosphatase PTEN and p53 are among the most common genetic abnormalities in high-grade glioma. Our proliferation analysis of various glioblastoma cell lines with different combinations of PTEN and p53 mutation status revealed that Wnt signaling plays an important role in tumor cell proliferation.

KEGG pathway expression profile analysis of U87MG cells revealed that Gpr177 depletion strongly interferes with the cell cycle machinery. Gpr177 silencing reduced the transcription of pro-proliferation associated Wnt target genes like cyclinD1, c-myc, PTMA and tenascin-C. It has been described that c-myc and cyclinD1 are associated with tumor proliferation and previous studies have identified that cyclinD1 regulates G1-to-S phase transition. The nuclear oncogenic protein PTMA is involved in cell proliferation but also in apoptotic activity and transcriptional regulation. PTMA expression is positively regulated by the transcription factor c-myc. Thus, downregulation of c-myc by Gpr177 depletion may contribute to reduced PTMA expression. Like other oncoproteins, tenascin-C overexpression correlates with a variety of cancer types and tumor cell lines. Tenascin-C is an extracellular matrix molecule, which modulates adhesion and is highly expressed in the microenvironment of most solid tumors. High tenascin-C expression correlates with malignancy in astrocytic tumors and leads to a poor patient survival prognosis. Previous studies revealed that tenascin-C expression is associated with proliferation and invasiveness of tumor cells. Reduced tenascin-C expression after Gpr177 silencing contributes to less mobility and invasion of Gpr177 targeted tumor cells.

Expression profile analysis of U87MG cells after Gpr177 silencing revealed a strong reduction in interleukin transcription. Signaling function of IL-6 and IL-8 have been analyzed in glioma cells concerning cell survival and tumor growth. High expression of IL-6 and IL-8 correlates with glioma malignancy through promotion of proliferation, survival and invasiveness. β-catenin silencing has no effect on interleukin expression indicating that β-catenin-independent Wnt signaling is important for transcriptional regulation of interleukins.

Collectively, the data indicate that Evi-mediated Wnt signaling performs an important function in proliferation, survival and migration of glioma cells. These functional characteristics play critical roles in the pathogenesis of human brain tumors and suggest that targeting Gpr177 may represent a potential strategy for therapeutic intervention. Considering that Gpr177 is a transmembrane component of the secretory pathway, interfering with Gpr177 enables blocking canonical and non-canonical Wnt signaling at early stages in tumor initiation.

The invention claimed is:

1. An antibody or antibody fragment that inhibits G protein-coupled receptor 177 (Gpr177), wherein the antibody or antibody fragment binds
   (a) the epitope H-FTSPKTPEHEGRYYNC-OH (SEQ ID NO:1)
   (b) an epitope comprising at least 3 consecutive amino acids of a) but being N- or C-terminal shifted in the corresponding Gpr177 amino acid sequence or
   (c) an epitope having at least 75% amino acid identity to the epitopes of (a) and/or (b).

2. The antibody or antibody fragment of claim 1, wherein the antibody or antibody fragment can alleviate cancer.

3. The antibody or antibody fragment of claim 2, wherein the cancer is selected from colon, liver, ovarian, thyroid, uterine, gastric, renal, neuroectodermal tissue cancer, melanoma, breast, or brain cancer.

4. The antibody or antibody fragment of claim 3, wherein the cancer is selected from glioma, malignant astrocytoma, glioblastoma, or medulloblastoma.

5. A pharmaceutical composition comprising an effective amount of an antibody or antibody fragment that inhibits Gpr177, wherein the antibody or antibody fragment binds
   (a) the epitope H-FTSPKTPEHEGRYYNC-OH (SEQ ID NO:1)
   (b) an epitope comprising at least 3 consecutive amino acids of a) but being N- or C-terminal shifted in the corresponding Gpr177 amino acid sequence or
   (c) an epitope having at least 75% amino acid identity to the epitopes of (a) and/or (b).

6. The pharmaceutical composition of claim 5, wherein the composition is effective for alleviating cancer.

7. The pharmaceutical composition of claim 6, wherein the the cancer is selected from colon, liver, ovarian, thyroid, uterine, gastric, renal, neuroectodermal tissue cancer, melanoma, breast, or brain cancer.

8. The pharmaceutical composition of claim 7, wherein the cancer is selected from glioma, malignant astrocytoma, glioblastoma, or medulloblastoma.

9. A kit comprising an antibody or antibody fragment that inhibits Gpr177, wherein the antibody or antibody fragment binds
   (a) the epitope H-FTSPKTPEHEGRYYNC-OH (SEQ ID NO:1)
   (b) an epitope comprising at least 3 consecutive amino acids of a) but being N- or C-terminal shifted in the corresponding Gpr177 amino acid sequence or
   (c) an epitope having at least 75% amino acid identity to the epitopes of (a) and/or (b).

* * * * *

SEQUENCE LISTING

<160> NUMBER OF SEQ ID NOS: 20

<210> SEQ ID NO 1
<211> LENGTH: 16
<212> TYPE: PRT
<213> ORGANISM: Homo sapiens

<400> SEQUENCE: 1

Phe Thr Ser Pro Lys Thr Pro Glu His Glu Gly Arg Tyr Tyr Asn Cys
 1               5                  10                  15

<210> SEQ ID NO 2
<211> LENGTH: 19
<212> TYPE: DNA
<213> ORGANISM: Artificial Sequence
<220> FEATURE:
<223> OTHER INFORMATION: Evi#1

<400> SEQUENCE: 2
acgaaucccu ucuacagua                                           19

<210> SEQ ID NO 3
<211> LENGTH: 19
<212> TYPE: DNA
<213> ORGANISM: Artificial Sequence
<220> FEATURE:
<223> OTHER INFORMATION: Evi#2

<400> SEQUENCE: 3
uaacggaagg ccauuggaa                                           19

<210> SEQ ID NO 4
<211> LENGTH: 20
<212> TYPE: DNA
<213> ORGANISM: Artificial Sequence
<220> FEATURE:
<223> OTHER INFORMATION: Evi#3

<400> SEQUENCE: 4
uaaaggauau ccgguugguu                                          20

<210> SEQ ID NO 5
<211> LENGTH: 19
<212> TYPE: DNA
<213> ORGANISM: Artificial Sequence
<220> FEATURE:
<223> OTHER INFORMATION: Control siRNA

<400> SEQUENCE: 5
gcugaaacau gcaguugua                                           19

<210> SEQ ID NO 6
<211> LENGTH: 19
<212> TYPE: DNA
<213> ORGANISM: Artificial Sequence
<220> FEATURE:
<223> OTHER INFORMATION: Control siRNA

<400> SEQUENCE: 6
gauaaaggcu acuguugga                                           19

<210> SEQ ID NO 7
<211> LENGTH: 19
<212> TYPE: DNA
<213> ORGANISM: Artificial Sequence
<220> FEATURE:

<223> OTHER INFORMATION: Control siRNA

<400> SEQUENCE: 7
ccacuaaugu ccagcguuu                                                        19

<210> SEQ ID NO 8
<211> LENGTH: 19
<212> TYPE: DNA
<213> ORGANISM: Artificial Sequence
<220> FEATURE:
<223> OTHER INFORMATION: siRNA against beta-catenin

<400> SEQUENCE: 8
acaaguagcu gauauugau                                                        19

<210> SEQ ID NO 9
<211> LENGTH: 22
<212> TYPE: DNA
<213> ORGANISM: Artificial Sequence
<220> FEATURE:
<223> OTHER INFORMATION: Primer Evi/Gpt177

<400> SEQUENCE: 9
tcatggtatt tcaggtgttt cg                                                    22

<210> SEQ ID NO 10
<211> LENGTH: 23
<212> TYPE: DNA
<213> ORGANISM: Artificial Sequence
<220> FEATURE:
<223> OTHER INFORMATION: probe#38, Roche

<400> SEQUENCE: 10
gcatgaggaa cttgaaccta aaa                                                   23

<210> SEQ ID NO 11
<211> LENGTH: 22
<212> TYPE: DNA
<213> ORGANISM: Artificial Sequence
<220> FEATURE:
<223> OTHER INFORMATION: beta-Catenin

<400> SEQUENCE: 11
agctagacca gctctctctt ca                                                    22

<210> SEQ ID NO 12
<211> LENGTH: 22
<212> TYPE: DNA
<213> ORGANISM: Artificial Sequence
<220> FEATURE:
<223> OTHER INFORMATION: probe #21, Roche

<400> SEQUENCE: 12
caatatcaag tccaagatca gc                                                    22

<210> SEQ ID NO 13
<211> LENGTH: 18
<212> TYPE: DNA
<213> ORGANISM: Artificial Sequence
<220> FEATURE:
<223> OTHER INFORMATION: Cyclin DI

<400> SEQUENCE: 13
gaagatcgtc gccacctg                                                         18

```
<210> SEQ ID NO 14
<211> LENGTH: 20
<212> TYPE: DNA
<213> ORGANISM: Artificial Sequence
<220> FEATURE:
<223> OTHER INFORMATION: probe #67, Roche

<400> SEQUENCE: 14
gacctcctcc tcgcacttct                                               20

<210> SEQ ID NO 15
<211> LENGTH: 18
<212> TYPE: DNA
<213> ORGANISM: Artificial Sequence
<220> FEATURE:
<223> OTHER INFORMATION: c-Myc

<400> SEQUENCE: 15
caccagcagc gactctga                                                 18

<210> SEQ ID NO 16
<211> LENGTH: 22
<212> TYPE: DNA
<213> ORGANISM: Artificial Sequence
<220> FEATURE:
<223> OTHER INFORMATION: probe #34, Roche

<400> SEQUENCE: 16
gatccagact ctgaccttt gc                                             22

<210> SEQ ID NO 17
<211> LENGTH: 20
<212> TYPE: DNA
<213> ORGANISM: Artificial Sequence
<220> FEATURE:
<223> OTHER INFORMATION: PTMA

<400> SEQUENCE: 17
cctgctaacg gggaatgtaa                                               20

<210> SEQ ID NO 18
<211> LENGTH: 23
<212> TYPE: DNA
<213> ORGANISM: Artificial Sequence
<220> FEATURE:
<223> OTHER INFORMATION: probe #75, Roche

<400> SEQUENCE: 18
cttcctcttc ttcgtctacc tca                                           23

<210> SEQ ID NO 19
<211> LENGTH: 18
<212> TYPE: DNA
<213> ORGANISM: Artificial Sequence
<220> FEATURE:
<223> OTHER INFORMATION: IL-8

<400> SEQUENCE: 19
atggttcctt ccggtggt                                                 18

<210> SEQ ID NO 20
<211> LENGTH: 20
<212> TYPE: DNA
<213> ORGANISM: Artificial Sequence
<220> FEATURE:
<223> OTHER INFORMATION: probe #72, Roche
```

```
<400> SEQUENCE: 20
agacagcaga gcacacaagc                                                   20
```